United States Patent
Thomas

(10) Patent No.: US 10,478,422 B1
(45) Date of Patent: *Nov. 19, 2019

(54) ORAL LIQUID COMPOSITIONS INCLUDING VALSARTAN

(71) Applicant: ECI Pharmaceuticals, LLC, Fort Lauderdale, FL (US)

(72) Inventor: Greg Thomas, Carrollton, GA (US)

(73) Assignee: ECI PHARMACEUTICALS, LLC, Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/224,229

(22) Filed: Dec. 18, 2018

Related U.S. Application Data

(63) Continuation-in-part of application No. 16/220,775, filed on Dec. 14, 2018.

(51) Int. Cl.
| | |
|---|---|
| *A61K 31/41* | (2006.01) |
| *A61K 9/00* | (2006.01) |
| *A61K 47/12* | (2006.01) |
| *A61P 9/04* | (2006.01) |
| *A61P 9/12* | (2006.01) |
| *A61K 9/08* | (2006.01) |

(52) U.S. Cl.
CPC .......... *A61K 31/41* (2013.01); *A61K 9/0053* (2013.01); *A61K 9/08* (2013.01); *A61K 47/12* (2013.01); *A61P 9/04* (2018.01); *A61P 9/12* (2018.01)

(58) Field of Classification Search
CPC ........ A61K 31/41; A61K 9/0053; A61K 9/08; A61K 47/12; A61P 9/12; A61P 9/04
See application file for complete search history.

(56) References Cited

U.S. PATENT DOCUMENTS

| | | |
|---|---|---|
| 5,399,578 A | 3/1995 | Buhlmayer et al. |
| 2007/0093542 A1 | 4/2007 | Rukhman et al. |
| 2010/0222334 A1* | 9/2010 | Talamonti ............ A61K 9/0095 514/224.2 |
| 2010/0267787 A1* | 10/2010 | Harasymiw .......... A61K 9/0053 514/381 |
| 2013/0102594 A1 | 4/2013 | Talamonti et al. |
| 2013/0109729 A1 | 5/2013 | Harasymiw et al. |

FOREIGN PATENT DOCUMENTS

WO    WO 2009/064681 A2    5/2009

OTHER PUBLICATIONS

Diovan (Diovan, Feb. 19, 2017). (Year: 2017).*
Prexxartan, Dec. 19, 2017 (Year: 2017).*

* cited by examiner

*Primary Examiner* — Umamaheswari Ramachandran
(74) *Attorney, Agent, or Firm* — K&L Gates LLP

(57) ABSTRACT

An aspect of the present disclosure is directed to an oral liquid composition comprising valsartan with enhanced solubility and stability. Other aspects are directed to methods of using the oral liquid compositions for the treatment of hypertension, treatment of heart failure and reduction of cardiovascular mortality in clinically stable patients with left ventricular failure or left ventricular dysfunction following myocardial infarction.

27 Claims, 8 Drawing Sheets

ORAL LIQUID COMPOSITIONS INCLUDING VALSARTAN

CROSS REFERENCE TO RELATED APPLICATION

This application claims priority as a continuation-in-part of co-pending U.S. patent application Ser. No. 16/220,775, filed on Dec. 14, 2018, the entire contents of which are hereby incorporated herein by reference.

FIELD OF THE INVENTION

Provided herein are oral liquid compositions including valsartan with enhanced solubility. Also provided herein, are methods of using oral liquid compositions including valsartan for the treatment of hypertension, treatment of heart failure and reduction of cardiovascular mortality in clinically stable patients with left ventricular failure or left ventricular dysfunction following myocardial infarction.

BACKGROUND

Valsartan is a nonpeptide, orally active, and specific angiotensin II receptor blocker acting on the $AT_1$ receptor subtype. Angiotensin II interacts with specific receptors on the surface of a target cell. It has been possible to identify receptor subtypes which are termed, e.g., $AT_1$- and $AT_2$-receptors. Significant efforts have been made to identify substances that bind to the $AT_1$-receptor. Such active ingredients are often termed angiotensin II antagonists. Because of the inhibition of the $AT_1$-receptor, such antagonists can be used, e.g., as antihypertensives or for the treatment of congestive heart failure. Angiotensin II antagonists are therefore understood to be those active ingredients which bind to the $AT_1$-receptor subtype. Prolonged and uncontrolled hypertensive vascular disease ultimately leads to a variety of pathological changes in target organs such as the heart and kidney. Sustained hypertension can lead an increased occurrence of stroke.

Valsartan is chemically described as N-(1-oxopentyl)-N-[[2'-(1H-tetrazol-5-yl)[1,1'-biphenyl]-4-yl]methyl]-L-valine. Valsartan is used for treating hypertension, treatment of heart failure and reduction of cardiovascular mortality in clinically stable patients with left ventricular failure or left ventricular dysfunction following myocardial infarction.

Valsartan is typically administered as a solid oral dosage form such as, for example, tablets, pills, and capsules. Oral ingestion is the most convenient and commonly employed route of drug delivery due to its ease of administration, high patient compliance, cost effectiveness, reduced sterility constraints, and flexibility in the design of dosage form.

However, some patients, specifically pediatric and geriatric patient populations, may dislike or have difficulty swallowing solid oral dosage forms, which can lead to associated disadvantages, such as patient non-compliance. In such situations, oral liquid dosage forms, including solutions, suspensions and emulsions, can be easier to administer and more suitable for use.

Many marketed pharmaceutical products do not have regulatory approval for pediatric use, resulting in "off-label" prescribing by physicians. When a pharmaceutical product does not have a labeled indication for children, manufacturers do not produce strengths and dosage forms appropriate for the pediatric population. Extemporaneously-prepared formulations are a sub-optimal option in instances where commercial liquid formulations are not available. At present, liquid dosage forms for valsartan are prepared by compounding tablets into a suspension. However, developing and compounding of pediatric formulations can be challenging for dispensing pharmacists, resulting in a variety of issues, including inaccurate dosing, poor stability, poor taste, adherence problems, and lack of standardizations in extemporaneous compounding. Consumers requiring a liquid dosage form may be putting themselves at risk since the product may not be made consistently from one pharmacist to another. Further, extemporaneously-prepared valsartan formulations have a short shelf life, typically a maximum shelf life of only 90 days.

Poor bioavailability of pharmaceuticals presents a major challenge in designing oral dosage forms. The oral bioavailability depends on several factors, including aqueous solubility, drug permeability, dissolution rate, first-pass metabolism, presystemic metabolism, and susceptibility to efflux mechanisms. The most frequent causes of low oral bioavailability are attributed to poor solubility and low permeability. For orally administered drugs, solubility is the most important rate limiting parameter to achieve their desired concentration in systemic circulation for pharmacological response. Accordingly, liquid compositions containing active pharmaceutical ingredients that are completely solubilized in a liquid composition are more advantageous over suspension compositions. The extent of solubility of a substance in a specific solvent is measured as the saturation concentration, at which the addition of more solute does not increase its concentration in the solution. The extent of solubility ranges widely, from infinitely soluble (fully miscible) (for example, ethanol in water) to poorly soluble (for example, silver chloride in water). Solubility is based on the highest-dose strength of an immediate release product. A drug is considered highly soluble when the highest dose strength is soluble in 250 mL or less of aqueous media over the pH range of 1 to 7.5.

Accordingly, there remains a need for a highly bioavailable, highly soluble, stable valsartan oral solution that can address these problems, while safely and effectively providing the proper and consistent administration of valsartan with accuracy and precision to patients who have difficulty swallowing solid dosage forms.

SUMMARY

Provided herein are stable oral liquid compositions including valsartan. In one aspect, the present disclosure provides an oral liquid composition comprising about 3.6 mg/mL to about 4.4 mg/mL valsartan, or a pharmaceutically acceptable salt or solvate thereof, wherein administration of a 320 mg dose of the oral liquid composition to a patient provides an in vivo plasma profile having a valsartan $AUC_{inf}$ between about 35,162 ng*hr/mL and about 72,130 ng*hr/mL is provided herein.

In another aspect, the present disclosure provides an oral liquid composition including about 3.6 mg/mL to about 4.4 mg/mL valsartan, or a pharmaceutically acceptable salt or solvate thereof, wherein administration of a dose of the oral liquid composition to a patient provides an in vivo plasma profile with a valsartan $AUC_{inf}$ within a range of about 114% to about 136% of the same dose from an oral tablet dosage form.

In another aspect, methods of administering an oral liquid composition including about 3.6 mg/mL to about 4.4 mg/mL valsartan are provided, wherein the methods achieve a valsartan $AUC_{inf}$ in the patient ranging from about 35,162 ng*hr/mL and about 72,130 ng*hr/mL.

In another aspect, oral liquid compositions comprising about 4 mg/mL valsartan or a pharmaceutically acceptable salt or solvate thereof, about 2 mg/mL potassium sorbate, about 10 mg/mL sodium citrate, and water are provided herein.

In some embodiments, the oral liquid compositions can further comprise about 2 mg/mL methylparaben. In various embodiments, the oral liquid compositions can further comprise about 0.2 mg/mL sucralose.

In some embodiments, the mole ratio of sodium citrate to valsartan is about 3.7:1 in the oral liquid compositions. In certain embodiments, the mole ratio of potassium sorbate to valsartan is about 1.5:1 in the oral liquid compositions. In various embodiments, the mole ratio of paraben to valsartan is about 1.4:1 in the oral liquid compositions. In some embodiments, the oral liquid composition is substantially free of solids.

In some embodiments, the pH of the oral liquid composition is about 5.8 to about 6.1. In certain embodiments, the sodium citrate can be or include sodium citrate dihydrate. In various embodiments, the pH of the oral liquid composition is about 6.0. In some embodiments, the total impurities in the oral liquid composition are not more than about 0.4%, by weight of the composition. In certain embodiments, the oral liquid composition is stable at a temperature ranging from about 20° C. to about 35° C. and a relative humidity ("RH") ranging from about 35% to about 75% for up to about 24 months.

In another aspect, methods of treating hypertension comprising administering to a patient in need thereof an oral liquid composition comprising about 4 mg/mL valsartan or a pharmaceutically acceptable salt or solvate thereof, about 2 mg/mL potassium sorbate, about 10 mg/mL sodium citrate, and water are provided herein.

In yet another aspect, methods of treating heart failure comprising administering to a patient in need thereof an oral liquid composition comprising about 4 mg/mL valsartan or a pharmaceutically acceptable salt or solvate thereof, about 2 mg/mL potassium sorbate, about 10 mg/mL sodium citrate, and water are provided herein.

In another aspect, methods of reducing cardiovascular mortality in clinically stable patients with left ventricular failure or left ventricular dysfunction following myocardial infarction are provided herein, the methods comprising administering to a patient in need thereof an oral liquid composition comprising about 4 mg/mL valsartan or a pharmaceutically acceptable salt or solvate thereof, about 2 mg/mL potassium sorbate, about 10 mg/mL sodium citrate, and water.

BRIEF DESCRIPTION OF THE DRAWINGS

Various features and characteristics of non-limiting and non-exhaustive embodiments disclosed and described in this specification may be better understood by reference to the accompanying figures, in which:

FIGS. 1A-1C are views of a 4 ounce glass container used to contain an oral liquid composition, as described herein, wherein FIG. 1A is an elevational view of the glass container, FIG. 1B is a plan view of a bottom of the glass container of FIG. 1A, and FIG. 1C is a detail of a threaded neck of the glass container shown in FIGS. 1A and 1B.

FIGS. 2A and 2B are views of a container closure system that can be used in conjunction with the container shown in FIGS. 1A-1C, wherein FIG. 2A is an exterior elevational view of a ribbed, threaded closure cap and FIG. 2B is a sectional view of the cap shown in FIG. 2A.

FIGS. 3A-3C are views of a 16 ounce glass container used to contain an oral liquid composition, as described herein, wherein FIG. 3A is a front elevational view of the glass container, FIG. 3B is a side elevational view of the glass container of FIG. 3A, and FIG. 3C is a detail of a threaded neck of the glass container shown in FIGS. 3A and 3B.

FIGS. 4A and 4B are views of a container closure system that can be used in conjunction with the container shown in FIGS. 3A-3C, wherein FIG. 4A is an exterior elevational view of a ribbed, threaded closure cap and FIG. 4B is a sectional view of the cap shown in FIG. 4A.

DETAILED DESCRIPTION

Figure 1A:
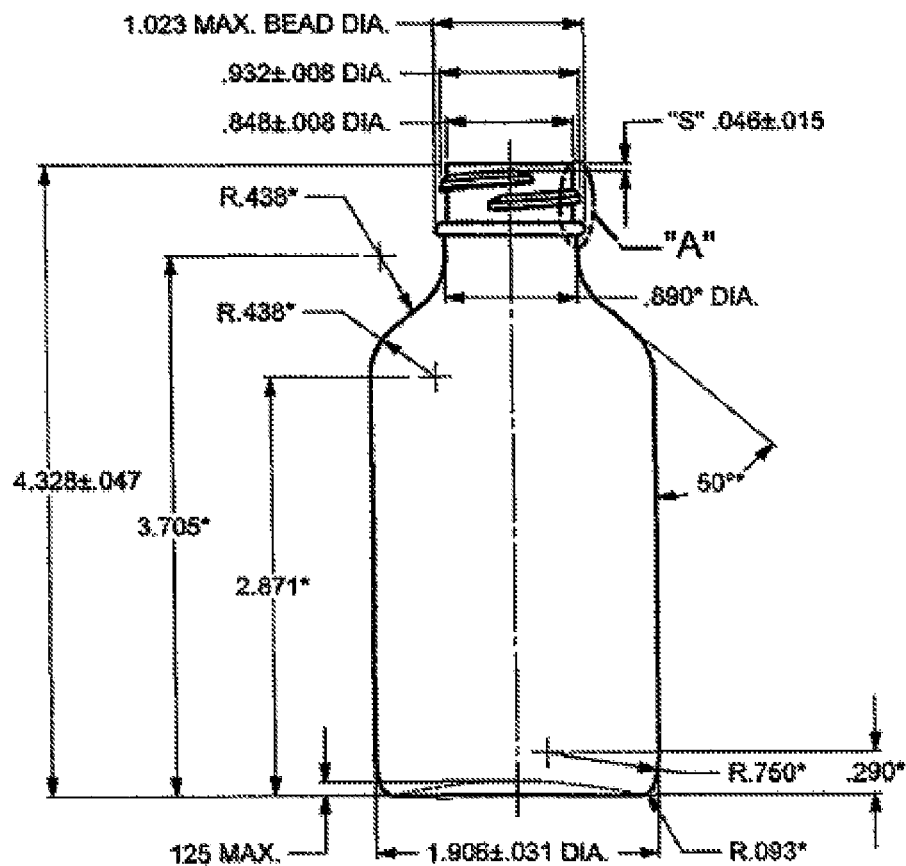

Provided herein are stable oral liquid compositions including valsartan. Such compositions can be useful in the treatment of hypertension, treatment of heart failure and reduction of cardiovascular mortality in clinically stable patients with left ventricular failure or left ventricular dysfunction following myocardial infarction. The compositions can provide advantages over conventional oral solid dosage administration of valsartan including, for example, ease of administration, improved absorption, increased patient compliance, and accurate/precise delivery of valsartan to the patient. Further, valsartan is fully solubilized in the oral liquid compositions, providing oral liquid compositions that have improved bioavailability over liquid compositions that are suspensions, in which valsartan is not fully solubilized.

As used herein the terms "suspension" and "suspensions" refer to liquid formulations in which the solute particles of a substance are suspended within a solvent and thus remain undissolved in the formulation. The degree to which a substance dissolves in a solvent to result in a solution is known as solubility. Solubility is the property of a solid, liquid, or gaseous chemical substance called a solute to dissolve in a solid, liquid or gaseous solvent. The solubility of a substance fundamentally depends on the physical and chemical properties of the solute and solvent, as well as on temperature, pressure, and presence of other chemicals (including changes to the pH) of the solution. As used herein, the phrase "fully solubilized" refers to the complete solubilization of a solute at a particular concentration in a solvent.

Certain segments of the population have difficulty ingesting and swallowing solid oral dosage forms. This often leads to non-compliance with the recommended therapy with solid dosage forms and can result in less-than-effective therapy. Moreover, an increased risk of choking can occur when children or the elderly take solid dosage forms.

Currently, a liquid alternative to solid oral dosage forms of valsartan can be prepared by a compounding pharmacist where valsartan solid dosage forms are mixed into a liquid. However, forming valsartan liquid compositions using such techniques can have significant drawbacks, including forming suspensions rather than solutions, large variability in the actual dosage amount of valsartan, incomplete or inconsistent suspension of the valsartan solid dosage form in the liquid, rapid instability, inconsistent formulation methods per compounding pharmacist, and several other potential issues.

It has now been discovered that an oral liquid valsartan composition that includes a citrate salt buffering agent and the sorbate salt and paraben preservatives, and having a pH of about 5.8 to about 6.1, surprisingly and unexpectedly provide markedly improved solubility of valsartan. For example, the inventors found that increasing the pH of the acidic valsartan composition from about 4 to about 6, increased the solubility of valsartan by a factor of about 1000. Further, such compositions exhibit surprising and unexpected stability up to about 18 months, or in some cases longer. In some embodiments, the oral liquid valsartan compositions exhibit a stability of up to 24 months or more.

Embodiments provided herein provide safe and effective administration of valsartan for the treatment of hypertension, treatment of heart failure, and reduction of cardiovascular mortality in clinically stable patients with left ventricular failure or left ventricular dysfunction following myocardial infarction.

As used herein, "valsartan" refers to any of valsartan base, its salt, solvate, derivative isomer or polymorph thereof. Suitable compounds include the free base, organic and inorganic salts, isomers, isomer salts, solvates, polymorphs, amorphous forms, complexes, etc. Valsartan can be purchased from commercial sources or can be prepared according to known methods such as, for example, methods described in U.S. Pat. No. 5,399,578 (incorporated herein by reference in its entirety). In certain embodiments, the valsartan used in compositions disclosed herein is or includes valsartan-free base. In various embodiments, the valsartan used in compositions disclosed herein is or includes a valsartan salt. In some embodiments, the valsartan used in compositions disclosed herein is or includes a solvate.

Oral Liquid Compositions Containing Valsartan:

In one aspect, certain oral liquid compositions comprise valsartan and a combination of citrate salt, sorbate salt, and a paraben are disclosed. The citrate salt is a buffering agent and the sorbate salt and paraben are preservatives, and they are present in the oral liquid compositions in ratios and amounts to provide an unexpectedly highly solubilized composition. Such oral liquid compositions also may be unexpectedly stable. In some embodiments, the oral liquid compositions are substantially free of solids, whereby all components are fully solubilized. The phrase "substantially free of solids", as used herein refers the characteristic wherein a solution is essentially or fundamentally devoid of solid particulates.

In some embodiments, valsartan is present in a concentration of about 3.6 mg/mL to about 4.4 mg/mL of the oral liquid composition, or at any value or in any range subsumed therein. In certain embodiments, valsartan is present in the oral liquid composition in a concentration ranging from about 3.0 mg/mL to about 5.0 mg/mL, about 3.2 mg/mL to about 4.8 mg/mL, about 3.5 mg/mL to about 4.5 mg/mL, about 3.6 mg/mL to about 4.4 mg/mL, about 3.7 mg/mL to about 4.3 mg/mL, about 3.9 mg/mL to about 4.1 mg/mL, about 3.5 mg/mL to about 4.1 mg/mL, about 3.6 mg/mL to about 4.1 mg/mL, about 3.7 mg/mL to about 4.1 mg/mL, about 3.8 mg/mL to about 4.2 mg/mL, about 3.6 mg/mL to about 4.2 mg/mL, or about 3.7 mg/mL to about 4.3 mg/mL of the oral liquid composition. In various embodiments, valsartan is present in a concentration of about 3.8 mg/mL, about 3.9 mg/mL, about 4 mg/mL, about 4.1 mg/mL, or about 4.2 mg/mL of the oral liquid composition. In certain embodiments, valsartan is present in a concentration of about 4.0 mg/mL of the oral liquid composition.

In some embodiments, valsartan is present in a concentration of from about 20% w/w to about 24% w/w of the total solids used to prepare the oral liquid composition, or at any concentration or within any concentration range subsumed therein. In certain embodiments, valsartan is present in a concentration of about 20.4% w/w to about 23.6% w/w of the total solids used to prepare the oral liquid composition. In various embodiments, valsartan is present in a concentration, by weight (w/w) of the total solids used to prepare the oral liquid composition, ranging from about 15% to about 25%, about 16% to about 24.5%, about 17% to about 24%, about 18% to about 223.9%, about 17% to about 23.9%, about 18% to about 23.9%, about 19% to about 23.8%, about 20% to about 23.8%, about 20.1% to about 23.8%, about 20.2% to about 23.8%, about 20.3% to about 23.7%, about 20.5% to about 23.7%, about 20.6% to about 23.6%, about 20.4% to about 23.5%, about 21.0% to about 23.0%, about 21.5% to about 23.5%, or about 20.3% to about 23.6%. In certain embodiments, valsartan is present in a concentration, by weight (w/w), of about 20.0% w/w, about 20.1% w/w, about 20.2% w/w, about 20.3% w/w, about 20.4% w/w, about 20.5% w/w, about 20.6% w/w, about 20.7% w/w, about 20.8% w/w, about 20.9% w/w, about 21.0% w/w, about 21.1% w/w, about 21.2% w/w, about 21.3% w/w, about 21.4% w/w, about 21.5% w/w, about 21.6% w/w, about 21.7% w/w, about 21.8% w/w, about 21.9% w/w, about 22.0% w/w, about 22.1% w/w, about 22.2% w/w, about 22.3% w/w, about 22.4% w/w, about 22.5% w/w, about 22.6% w/w, about 22.7% w/w, about 22.8% w/w, about 22.9% w/w, about 23.0% w/w, about 23.1% w/w, about 23.2% w/w, about 23.3% w/w, about 23.4% w/w, about 23.5% w/w, about 23.6% w/w, about 23.7% w/w, about 23.8% w/w, about 23.9% w/w, or about 24.0% w/w of the total solids used to prepare the oral liquid composition.

In some embodiments, the oral liquid composition has a pH of about 5.8 to about 6.2, or at any value or in any range subsumed therein. In other embodiments, the oral liquid composition has a pH of about 5.9 to about 6.1. In certain embodiments, the oral liquid composition has a pH ranging from about 5.0 to about 7.0, about 5.1 to about 6.9, about 5.2 to about 6.8, about 5.3 to about 6.7, about 5.4 to about 6.6, about 5.5 to about 6.5, about 5.6 to about 6.4, about 5.7 to about 6.3, about 5.9 to about 6.1. In various embodiments, the oral liquid composition has a pH of about 5.8, about 5.9, about 6.0, about 6.1, or about 6.2.

In some embodiments of the oral liquid composition, the citrate salt is or includes a group IA or group 2A salt. In certain embodiments, the citrate salt is or includes sodium citrate, potassium citrate, calcium citrate, magnesium citrate, or hydrates, solvates or anhydrous forms thereof. In various embodiments, the citrate salt is or includes sodium citrate. In some embodiments, the citrate salt is or includes monosodium citrate, disodium citrate, trisodium citrate, trisodium citrate dihydrate, anhydrous trisodium citrate, disodium hydrogen citrate, disodium citrate sesquihydrate, calcium citrate, or magnesium citrate. In some embodiments, the citrate salt is or includes sodium citrate dihydrate.

In some embodiments, the citrate salt is present in the oral liquid composition in amounts sufficient to provide a pH of about 5.8 to about 6.2, or at any value or in any range subsumed therein. In certain embodiments, the citrate salt is present in the oral liquid composition in amounts sufficient to provide a pH of about 5.2 to about 6.8, about 5.3 to about 6.7, about 5.4 to about 6.6, about 5.3 to about 6.5, about 5.4 to about 6.4, about 5.5 to about 6.3, about 5.6 to about 6.3, about 5.7 to about 6.2, or about 5.9 to about 6.1. In various embodiments, the citrate salt is present in the oral liquid composition in an amount sufficient to provide a pH of about 5.8, about 5.9, about 6.0, about 6.1, or about 6.2.

In some embodiments, sodium citrate is present in a concentration of from about 9.8 mg/mL to about 10.2 mg/mL of the oral liquid composition, or in any concentration or within any concentration range subsumed therein. In certain embodiments, sodium citrate is present in a concentration of from about 9.3 mg/mL to about 10.7 mg/mL, about 9.4 mg/mL to about 10.6 mg/mL, about 9.5 mg/mL to about 10.5 mg/mL, about 9.6 mg/mL to about 10.4 mg/mL, about 9.7 mg/mL to about 10.3 mg/mL, about 9.9 mg/mL to about 10.2 mg/mL, about 9.8 mg/mL to about 10.3 mg/mL, or about 9.9 mg/mL to about 10.1 mg/mL of the oral liquid composition. In various embodiments, sodium citrate is present in a concentration of about 9.8 mg/mL, about 9.9 mg/mL, about 10.0 mg/mL, about 10.1 mg/mL, or about 10.2 mg/mL of the oral liquid composition. In some embodiments, sodium citrate is present in a concentration of about 10.0 mg/mL of the oral liquid composition.

In some embodiments, sodium citrate is present in a concentration of from about 52% w/w to about 58% w/w of the total solids used to prepare the oral liquid composition, or in any concentration or within any concentration range subsumed therein. In other embodiments, sodium citrate is present a concentration of from about 52.6% w/w to about 57.4% w/w of the total solids used to prepare the oral liquid composition. In various embodiments, sodium citrate is present in a concentration of from about 48% to about 62%, about 49% to about 61%, about 50% to about 60%, about 51% to about 59%, about 52% to about 60%, about 52% to about 61%, about 50% to about 58%, about 51% to about 58%, about 52.1% to about 57.1%, about 52.2% to about 57.2%, about 52.3% to about 57.6%, about 52.4% to about 57.5%, about 52.5% to about 57.7%, or about 52.3% to about 57.5% w/w of the total solids used to prepare the oral liquid composition. In certain embodiments, sodium citrate is present in a concentration of about 52.0% w/w, about 52.1% w/w, about 52.2% w/w, about 52.3% w/w, about 52.4% w/w, about 52.5% w/w, about 52.6% w/w, about 52.7% w/w, about 52.8% w/w, about 52.9% w/w, about 53.0% w/w, about 53.1% w/w, about 53.2% w/w, about 53.3% w/w, about 53.4% w/w, about 53.5% w/w, about 53.6% w/w, about 53.7% w/w, about 53.8% w/w, about 53.9% w/w, about 54.0% w/w, about 54.1% w/w, about 54.2% w/w, about 54.3% w/w, about 54.4% w/w, about 54.5% w/w, about 54.6% w/w, about 54.7% w/w, about 54.8% w/w, about 54.9% w/w, about 55.0% w/w, about 55.1% w/w, about 55.2% w/w, about 55.3% w/w, about 55.4% w/w, about 55.5% w/w, about 55.6% w/w, about 55.7% w/w, about 55.8% w/w, about 55.9% w/w, about 56.0% w/w, about 56.1% w/w, about 56.2% w/w, about 56.3% w/w, about 56.4% w/w, about 56.5% w/w, about 56.6% w/w, about 56.7% w/w, about 56.8% w/w, about 56.9% w/w, about 57.0% w/w, about 57.1% w/w, about 57.2% w/w, about 57.3% w/w, about 57.4% w/w, about 57.5% w/w, about 57.6% w/w, about 57.7% w/w, about 57.8% w/w, about 57.9% w/w, or about 58.0% w/w of the total solids used to prepare the oral liquid composition.

In some embodiments of the oral liquid composition, the sorbate salt incorporated therein is or includes a group IA or a group IIA salt. In other embodiments, the sorbate salt is or includes lithium sorbate, potassium sorbate, sodium sorbate, calcium sorbate, or magnesium sorbate. In some embodiments, the sorbate salt is present in an amount sufficient to provide a stable composition, for example, providing antimicrobial activity that prevents growth and/or spread of bacteria and molds. In some embodiments, the sorbate salt is present in a concentration of from about 1 mg/mL to about 3 mg/mL of the oral liquid composition, or in any concentration or within any concentration range subsumed therein. In certain embodiments, the sorbate salt is present in a concentration of from about 0.8 mg/mL to about 3.2 mg/mL, about 0.9 mg/mL to about 3.1 mg/mL, about 1.1 mg/mL to about 2.9 mg/mL, about 1.2 mg/mL to about 2.8 mg/mL, about 1.3 mg/mL to about 2.7 mg/mL, about 1.4 mg/mL to about 2.6 mg/mL, about 1.5 mg/mL to about 2.5 mg/mL, about 1.5 mg/mL to about 2.4 mg/mL, about 1.6 mg/mL to about 2.3 mg/mL, about 1.7 mg/mL to about 2.3 mg/mL, about 1.8 mg/mL to about 2.2 mg/mL, about 1.9 mg/mL to about 2.1 mg/mL, about 1.6 mg/mL to about 2.2 mg/mL, or about 1.8 mg/mL to about 2.5 mg/mL of the oral liquid composition.

In some embodiments, the sorbate salt is or includes potassium sorbate. In certain embodiments, potassium sorbate is present in a concentration of from about 1.8 mg/mL to about 2.2 mg/mL of the oral liquid composition, or in any concentration or within any concentration range subsumed therein. In certain embodiments, the potassium sorbate is present in a concentration of from about 0.8 mg/mL to about 3.2 mg/mL, about 0.9 mg/mL to about 3.1 mg/mL, about 1.1 mg/mL to about 2.9 mg/mL, about 1.2 mg/mL to about 2.8 mg/mL, about 1.3 mg/mL to about 2.7 mg/mL, about 1.4 mg/mL to about 2.6 mg/mL, about 1.5 mg/mL to about 2.5 mg/mL, about 1.5 mg/mL to about 2.4 mg/mL, about 1.6 mg/mL to about 2.3 mg/mL, about 1.7 mg/mL to about 2.3 mg/mL, about 1.8 mg/mL to about 2.2 mg/mL, about 1.9 mg/mL to about 2.1 mg/mL, about 1.6 mg/mL to about 2.2 mg/mL, or about 1.8 mg/mL to about 2.5 mg/mL of the oral liquid composition. In various embodiments, potassium sorbate is present in a concentration of about 1.8 mg/mL, about 1.9 mg/mL, about 2.0 mg/mL, about 2.1 mg/mL, or about 2.2 mg/mL of the oral liquid composition.

In some embodiments, the sorbate salt is present in a concentration of from about 5% w/w to about 15% w/w of the total solids used to prepare the oral liquid composition, or in any concentration or within any concentration range subsumed therein. In certain embodiments, the sorbate salt is present in a concentration of from about 9% w/w to about 13% w/w of the total solids used to prepare the oral liquid composition. In certain embodiments, the sorbate salt is present in a concentration of from about 4% w/w to about 16% w/w, about 6% w/w to about 14% w/w, about 7% w/w to about 13% w/w, about 8% w/w to about 15% w/w, about 9% w/w to about 14% w/w, about 10.5% w/w to about 11.5% w/w, about 11% w/w to about 13% w/w, or about 10% w/w to about 13% w/w of the total solids used to prepare the oral liquid composition. In various embodiments, the sorbate salt is present in a concentration of from about 10% w/w to about 12% w/w of the total solids used to prepare the oral liquid composition.

In some embodiments, potassium sorbate is present in a concentration of from about 9.5% w/w to about 12.5% w/w of the total solids used to prepare the oral liquid composition, or in any concentration or within any concentration range subsumed therein. In certain embodiments, potassium sorbate is present in a concentration of from about 9.0% w/w to about 13% w/w, about 9.1% w/w to about 12.9% w/w, about 9.2% w/w to about 12.8% w/w, about 9.3% w/w to about 12.7% w/w, about 9.4% w/w to about 12.6% w/w, about 9.6% w/w to about 12.5% w/w, about 9.7% w/w to about 12.4% w/w, about 9.8% w/w to about 12.4% w/w, about 9.9% w/w to about 12.3% w/w, or about 10% w/w to about 13% w/w of the total solids used to prepare the oral liquid composition. In some embodiments, potassium sorbate is present in a concentration of about 9.5% w/w, about 9.6% w/w, about 9.7% w/w, about 9.8% w/w, about 9.9% w/w, about 10.0% w/w, about 10.1% w/w, about 10.2% w/w, about 10.3% w/w, about 10.4% w/w, about 10.5% w/w, about 10.6% w/w, about 10.7% w/w, about 10.8% w/w, about 10.9% w/w, about 11.0% w/w, about 11.1% w/w, about 11.2% w/w, about 11.3% w/w, about 11.4% w/w, about 11.5% w/w, about 11.6% w/w, about 11.7% w/w, about 11.8% w/w, about 11.9% w/w, about 12.0% w/w, about 12.1% w/w, about 12.2% w/w, about 12.3% w/w, about 12.4% w/w, or about 12.5% w/w of the total solids used to prepare the oral liquid composition.

In some embodiments of the oral liquid composition, the paraben is or includes methylparaben, ethylparaben, propylparaben, or butylparaben. In certain embodiments, the paraben is present in an amount sufficient to provide a stable oral liquid composition, for example, providing anti-microbial activity that prevents growth and/or spread of bacteria and molds. In various embodiments, the paraben is present in a concentration of from about 1 mg/mL to about 3 mg/mL of the oral liquid composition, or in any concentration or within any concentration range subsumed therein. In certain embodiments, the paraben is present in a concentration of from about 0.5 mg/mL to about 4 mg/mL, 0.6 mg/mL to about 3.9 mg/mL, 0.7 mg/mL to about 3.8 mg/mL, 0.8 mg/mL to about 3.7 mg/mL, about 0.9 mg/mL to about 3.6, about 1.1 mg/mL to about 2.9 mg/mL, about 1.2 mg/mL to about 2.8 mg/mL, about 1.3 mg/mL to about 2.7 mg/mL, about 1.4 mg/mL to about 2.6 mg/mL, or about 1.5 mg/mL to about 2.5 mg/mL of the oral liquid composition.

In some embodiments of the oral liquid composition, the paraben is or includes methylparaben. In certain embodiments, methylparaben is present in a concentration of from about 1.8 mg/mL to about 2.2 mg/mL of the oral liquid composition, or in any concentration or within any concentration range subsumed therein. In certain embodiments, the methylparaben is present in a concentration of from about 1.1 mg/mL to about 2.9 mg/mL, about 1.2 mg/mL to about 2.8 mg/mL, about 1.3 mg/mL to about 2.7 mg/mL, about 1.4 mg/mL to about 2.6 mg/mL, about 1.5 mg/mL to about 2.5 mg/mL, about 1.7 mg/mL to about 2.3 mg/mL, or about 1.9 mg/mL to about 2.1 mg/mL of the oral liquid composition. In various embodiments, methylparaben is present in a concentration of about 1.8 mg/mL, about 1.9 mg/mL, about 2.0 mg/mL, about 2.1 mg/mL, or about 2.2 mg/mL of the oral liquid composition.

In some embodiments, the paraben is present in a concentration of from about 5% w/w to about 15% w/w of the total solids used to prepare the oral liquid composition, or in any concentration or within any concentration range subsumed therein. In certain embodiments, the paraben is present in a concentration of from about 9% w/w to about 13% w/w of the total solids used to prepare the oral liquid composition. In certain embodiments, the paraben is present in a concentration of from about 4% w/w to about 16% w/w, about 4.5% w/w to about 15.5% w/w, about 6% w/w to about 14% w/w, about 7% w/w to about 13% w/w, about 8% w/w to about 15% w/w, about 9% w/w to about 14% w/w, about 10% w/w to about 13% w/w, about 10.5% w/w to about 11.5% w/w, or about 11% w/w to about 13% w/w of the total solids used to prepare the oral liquid composition. In yet other embodiments, the paraben is present in a concentration of from about 10% w/w to about 12% w/w of the total solids used to prepare the oral liquid composition.

In other embodiments, methylparaben is present in a concentration of from about 9.5% w/w to about 12.5% w/w of the total solids used to prepare the oral liquid composition, or in any concentration or in any concentration range subsumed therein. In certain embodiments, methylparaben is present in a concentration of from about 9.0% w/w to about 13% w/w, about 9.1% w/w to about 12.9% w/w, about 9.2% w/w to about 12.8% w/w, about 9.3% w/w to about 12.7% w/w, about 9.4% w/w to about 12.6% w/w, about 9.6% w/w to about 12.5% w/w, or about 9.7% w/w to about 12.4% w/w, about 9.8% w/w to about 12.4% w/w, about 9.9% w/w to about 12.3% w/w, or about 10% w/w to about 13% w/w of the total solids used to prepare the oral liquid composition. In some embodiments, methylparaben is present in a concentration of about 9.5% w/w, about 9.6% w/w, about 9.7% w/w, about 9.8% w/w, about 9.9% w/w, about 10.0% w/w, about 10.1% w/w, about 10.2% w/w, about 10.3% w/w, about 10.4% w/w, about 10.5% w/w, about 10.6% w/w, about 10.7% w/w, about 10.8% w/w, about 10.9% w/w, about 11.0% w/w, about 11.1% w/w, about 11.2% w/w, about 11.3% w/w, about 11.4% w/w, about 11.5% w/w, about 11.6% w/w, about 11.7% w/w, about 11.8% w/w, about 11.9% w/w, about 12.0% w/w, about 12.1% w/w, about 12.2% w/w, about 12.3% w/w, about 12.4% w/w, or about 12.5% w/w of the total solids used to prepare the oral liquid composition.

In some embodiments of the oral liquid composition, the mole ratio of citrate salt to valsartan is from about 3:1 to about 4:1. In certain embodiments, the mole ratio of citrate salt to valsartan is about 3:1, about 3.1:1, about 3.2:1, about 3.3:1, about 3.4:1 about 3.5:1, about 3.6:1, about 3.7:1, about 3.8:1, about 3.9:1, or about 4:1. In various embodiments, the mole ratio of citrate salt to valsartan is about 3.7:1.

In some embodiments of the oral liquid composition, the mole ratio of sorbate salt to valsartan is from about 1:1 to about 2:1. In certain embodiments, the mole ratio of sorbate salt to valsartan is about 1:1, about 1.1:1, about 1.2:1, about 1.3:1, about 1.4:1, about 1.5:1, about 1.6:1, about 1.7:1, about 1.8:1, about 1.9:1, about 2:1, about 2.1:1, about 2:1.1, or about 2.1:1.1. In various embodiments, the mole ratio of sorbate salt to valsartan is about 1.5:1.

In some embodiments of the oral liquid composition, the mole ratio of paraben to valsartan is from about 1:1 to about 2:1. In certain embodiments, the mole ratio of paraben to valsartan is about 1:1, about 1.1:1, about 1.2:1, about 1.3:1, about 1.4:1, about 1.5:1, about 1.6:1, about 1.7:1, about 1.8:1, about 1.9:1, about 2:1, about 2.1:1, about 2:1.1, or about 2.1:1.1. In various embodiments, the mole ratio of paraben to valsartan is about 1.4:1.

In some embodiments of the oral liquid composition, the mole ratio of citrate salt to sorbate salt is from about 2:1 to about 3:1. In certain embodiments, the mole ratio of citrate salt to sorbate salt is about 2:1, about 2.1:1, about 2.2:1, about 2.3:1, about 2.4:1, about 2.5:1, about 2.6:1, about 2.7:1, about 2.8:1, about 2.9:1, about 2.9:1.1, about 3:1, about 3:1.1, about 3.1:1, or about 3.1:1.1. In various embodiments, the mole ratio of citrate salt to sorbate salt is about 2.6:1.

In some embodiments of the oral liquid composition, the mole ratio of citrate salt to paraben is from about 2:1 to about 3:1. In certain embodiments, the mole ratio of citrate salt to paraben is about 2:1, about 2.1:1, about 2.2:1, about 2.3:1, about 2.4:1, about 2.5:1, about 2.6:1, about 2.7:1, about 2.8:1, about 2.9:1, about 2.9:1.1, about 3:1, about 3:1.1, about 3.1:1, or about 3.1:1.1. In various embodiments, the mole ratio of citrate salt to paraben is about 2.6:1.

In some embodiments of the oral liquid composition, the mole ratio of sorbate salt to paraben is from about 0.5:1 to about 1.5:1. In certain embodiments, the mole ratio of sorbate salt to paraben is from about 0.6:1, about 0.7:1, about 0.8:1, about 1.1:1, about 1.2:1, about 1.3:1, 1.4:1, about 1.6:1, about 1.7:1, about 1.8:1, about 1.9:1, or about 2:1. In various embodiments, the mole ratio of sorbate salt to paraben is about 1:1.

In some embodiments, the oral liquid composition can comprise one or more additional excipients, including but not limited to, sweeteners, flavoring agents, stabilizers, coloring agents, thickeners and the like. Additional excipients can be selected based on function and compatibility with the oral liquid composition disclosed herein and may be found, for example, in Remington: The Science and Practice of Pharmacy, Nineteenth Ed. (Easton, Pa.: Mack Publishing Company, 1995); Hoover, John E., Remington's Pharmaceutical Sciences, (Easton, Pa.: Mack Publishing Company, 1975); Liberman, H. A. and Lachman, L., Eds., Pharmaceutical Dosage Forms (New York, N.Y.: Marcel Decker, 1980); and Pharmaceutical Dosage Forms and Drug Delivery Systems, Seventh Ed. (Lippincott Williams & Wilkins, 1999), Kibbe, Arthur H., "Handbook of Pharmaceutical Excipients" (3rd ed.) (2000) all of which are herein incorporated by reference in their entirety.

One or more sweeteners or sweetening agents can be used in the liquid composition and can include any compounds that provide a sweet taste, including, for example, natural and synthetic sugars, natural and artificial sweeteners, natural extracts and any material that initiates a sweet sensation in a subject. In some embodiments, the oral liquid composition disclosed herein comprises one or more sweeteners. In some embodiments, solid, powder sweeteners are used in the liquid composition disclosed herein. In other embodiments, sweeteners in liquid form, also referred to as syrups, are used in the oral liquid composition disclosed herein.

Suitable sweeteners for inclusion in the oral liquid composition include, but are not limited to, glucose, fructose, sucrose, xylitol, tagatose, sucralose, maltitol, isomaltulose, ISOMALT™ (hydrogenated isomaltulose), lactitol, sorbitol, mannitol, erythritol, trehalose, maltodextrin, polydextrose, and the like. Other sweeteners that may be included in the compositions herein include, for example, glycerin, inulin, erythritol, maltol, acesulfame and salts thereof (e.g., acesulfame potassium), alitame, aspartame, neotame, sodium cyclamate, saccharin and salts thereof (e.g., saccharin sodium or saccharin calcium), neohesperidin dihydrochalcone, stevioside, thaumatin, and the like. Sweeteners can be used in the form of crude or refined products, such as, for example, hydrogenated starch hydrolysates, maltitol syrup, high fructose corn syrup, etc., and as branded products, e.g., SWEET AM™ liquid (Product Code 918.003—propylene glycol, ethyl alcohol, and proprietary artificial flavor combination, Flavors of North America), SWEET AM™ powder (Product Code 918.005—maltodextrin, sorbitol, and fructose combination and Product Code 918.010—water, propylene glycol, sorbitol, fructose, and proprietary natural and artificial flavor combination, Flavors of North America), PROSWEET™ (1-10% proprietary plant/vegetable extract and 90-99% dextrose combination, Virginia Dare), MALTISWEET™ (maltitol solution, Ingredion) and SORBO™ (sorbitol and sorbitol/xylitol solution, SPI Polyols), INVERTOSE™ (high fructose corn syrup, Ingredion), and ORA-SWEET™ sugar-free flavored syrup (Paddock Laboratories, Inc.). Sweeteners can be used singly or in combinations of two or more. In some embodiments, the sweetener is sucralose. Suitable concentrations of different sweeteners can be selected based on published information, manufacturers' data sheets, and/or by routine testing.

In some embodiments of the oral liquid composition, the sweetener is present in an amount equivalent to about 0.01% w/w to about 5% w/w of the total solids used to prepare the liquid composition, or in any concentration or within any concentration range subsumed therein. In certain embodiments, the sweetener is present in an amount equivalent to about 0.5% w/w to about 2.5% w/w of the total solids used to prepare the liquid composition. In certain embodiments, the sweetener is present in a concentration of from about 0.2% w/w to about 4.5% w/w, about 0.3% w/w to about 4% w/w, about 0.4% w/w to about 3.5% w/w, about 0.5% w/w to about 3% w/w, or about 0.6% w/w to about 2.6% w/w. In various embodiments, the sweetener is present in a concentration of from about 1% w/w to about 2% w/w of the total solids used to prepare the liquid composition.

In some embodiments of the oral liquid composition, the sweetener is or includes sucralose. In certain embodiments, sucralose is present in the oral liquid composition in a concentration of from about 0.1 mg/mL, to about 0.3 mg/mL, or in any concentration or within any concentration range subsumed therein. In various embodiments, sucralose is present in the oral liquid composition in a concentration of a range of from about 0.05 mg/mL to about 0.5 mg/mL, about 0.07 mg/mL to about 0.45 mg/mL, about 0.09 mg/mL, to about 0.4 mg/mL, about 0.14 mg/mL to about 0.35 mg/mL, about 0.16 mg/mL to about 0.3 mg/mL, about 0.17 mg/mL to about 0.27 mg/mL, or about 0.13 mg/mL to about 0.20 mg/mL. In certain embodiments, sucralose is present in a concentration of from about 0.15 mg/mL to about 0.25 mg/mL. In various embodiments, sucralose is present in a concentration of about 0.15 mg/mL, about 0.16 mg/mL, about 0.17 mg/mL, about 0.18 mg/mL, about 0.19 mg/mL, about 0.20 mg/L, about 0.21 mg/mL, about 0.22 about 0.23 mg/mL, about 0.24 mg/mL, or about 0.25 mg/mL.

In some embodiments of the oral liquid composition, sucralose is present in a concentration of from about 0.5% w/w to about 2% w/w of the total solids used to prepare the oral liquid composition, or in any concentration or within any concentration range subsumed therein. In certain embodiments, sucralose is present in a concentration of from about 0.9% w/w to about 1.3% w/w of the total solids used to prepare the oral liquid composition. In various embodiments, the oral liquid composition includes sucralose in a concentration range, by weight, of from about 0.3% w/w to about 3% w/w, about 0.4% w/w to about 2.7% w/w, about 0.4% w/w to about 5% w/w, about to about 2% w/w, about to about 1.8% w/w, about 0.8% w/w to about 1.5% w/w, or about 1% to about 2.1% w/w of the total solids used to prepare the oral liquid composition. In various embodiments, sucralose is present in a concentration of about 0.9% w/w, about 1.0% w/w, about 1.1% w/w, about 1.2% w/w, or about 1.3% w/w of the total solids used to prepare the oral liquid composition.

One or more flavoring agents can be used to enhance the taste or aroma of the oral liquid composition. Suitable natural or synthetic flavoring agents can be selected from standard reference books, for example Fenaroli's Handbook of Flavor Ingredients, 3rd edition (1995). Non-limiting examples of suitable natural flavors for inclusion in the oral liquid composition, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, tutti-frutti, vanilla, wintergreen, and the like. In certain embodiments, flavoring agents include cherry, grape, and bubblegum. In some embodiments, the liquid composition comprises a grape flavoring agent.

In some embodiments, the flavoring agent is present in a concentration of from about 1 mg/mL to about 5 mg/mL of the oral liquid composition, or in any concentration or within any concentration range subsumed therein. In certain embodiments, the flavoring agent is present in the oral liquid composition in a concentration ranging from about 1.4 mg/mL to about 3 mg/mL, about 2 mg/mL to about 4 mg/mL, about 2.2 mg/mL to about 3.7 mg/mL, or about 2.8 mg/mL to about 3.7 mg/mL. In various embodiments, the flavoring agent is present in the oral liquid composition in a concentration ranging from about 2.5 mg/mL to about 3.5 mg/mL.

Coloring agents can be included in the composition herein for identification and/or aesthetic purposes. Suitable coloring agents include, but are not limited to, FD&C Red No. 3, FD&C Red No. 20, FD&C Red No. 40, FD&C Yellow No. 6, FD&C Blue No. 2, D&C Green No. 5, D&C Orange No. 5, caramel, ferric oxide, or mixtures thereof.

The oral liquid compositions disclosed herein may be prepared in the forms of, for example and without limitation, aqueous solutions, nonaqueous solutions, juices, elixirs, and the like. Despite valsartan having low solubility, the oral liquid compositions herein surprisingly are solutions rather than suspensions, wherein no active ingredient is present as particulate matter or in a solid form in the compositions. Fully solubilizing the active ingredients, such as valsartan, in the oral liquid compositions herein provides advantages over their partially solubilized counterparts (e.g., suspensions, slurries etc.). Such advantages include, for example, higher drug absorption and drug permeability, lending to improved bioavailability. However, low solubility active ingredients, such as valsartan, typically pose significant challenges to formulating liquid compositions in which the active ingredient is completely soluble and remains completely soluble until administration. The oral liquid compositions disclosed herein overcome those challenges.

Suitable liquid vehicles for use in the oral liquid compositions herein are selected based on imparting desired qualities, including for example, clarity, nontoxicity, acceptable viscosity, compatibility with excipients, chemical inertness, palatability, acceptable odor and color, and economy. Exemplary liquid vehicles include, for example, water, ethyl alcohol, glycerin, propylene glycol, syrup (sugar or other sweetener based substance, e.g., ORA-SWEET™ SF sugar-free flavored syrup), juices (apple, grape, orange, cranberry, cherry, tomato and the like), other beverages (tea, coffee, soft drinks, milk and the like), oils (olive, soybean, corn, mineral, castor and the like), and combinations or mixtures thereof. Certain liquid vehicles, e.g., one or more oils and water, can be combined to form emulsions for inclusion in the oral liquid composition. In some embodiments, water is used as a vehicle in the oral liquid composition. In certain embodiments, a syrup is used as a vehicle in the oral liquid composition. In various embodiments, a juice is used as a vehicle in the oral liquid composition.

In some embodiments, the oral liquid composition disclosed herein is homogenous. As used herein, a "homogenous liquid" refers to a liquid that is uniform in appearance, identity, consistency and drug concentration per volume. Non-homogenous liquids include such liquids that have varied coloring, and/or viscosity, as well as non-uniform drug concentration in each unit volume. Homogeneity in liquids is assessed by qualitative identification or appearance tests and/or quantitative High Performance Liquid Chromatography (HPLC) testing or the like. Exemplary qualitative testing includes visual inspection of the resultant liquid for air bubbles and/or undissolved solids which may cause variable dosing. Analytical HPLC testing can also determine drug concentration uniformity by examining aliquots of certain volume sections (e.g., 5 or 10 mL from the top, middle and bottom of a 150 mL bottle). The mixing methods and excipients disclosed herein are selected to impart a homogenous quality to the oral liquid composition.

Mixing methods encompass any type of mixing resulting in a homogenous oral liquid composition. Mixing can include one or more of stirring, shaking, swirling, agitating, or inverting. In some embodiments, individual components of the oral liquid composition are added sequentially, concurrently, or in any combination thereof to a liquid vehicle. In some embodiments, individual components are added sequentially, one at a time. In certain embodiments, the sequential addition of individual components includes mixing for a certain time interval after each or some of the sequential additions. In various embodiments, all individual components are added at the same time to a liquid vehicle and then mixed for a certain time interval.

In various embodiments disclosed herein, mixing occurs for certain time intervals, such as, for example, about 10 seconds, about 20 seconds, about 30 seconds, about 40 seconds, about 50 seconds, about 60 seconds, about 90 seconds, about 2 minutes, about 2.5 minutes, about 3 minutes, about 3.5 minutes, about 4 minutes, about 4.5 minutes, about 5 minutes, about 6 minutes, about 7 minutes, about 8 minutes, about 9 minutes or about 10 minutes or more. In certain embodiments, mixing occurs in time interval ranges, for example, from about 10 seconds to about 60 seconds, about 30 seconds to about 60 seconds, about 1 minute to about 10 minutes, about 3 minutes to about 7 minutes, or about 5 minutes to about 10 minutes. In embodiments where there are two or more mixing steps, the time intervals for each mixing can be the same or different. In some embodiments, the resulting oral liquid composition is allowed to stand for a set amount of time, for example, about 5 minutes, about 10 minutes, about 20 minutes, about 30 minutes, about 40 minutes, about 50 minutes, about 60 minutes, about 90 minutes, about 120 minutes, or more to allow any resulting air bubbles arising from mixing to dissipate.

The oral liquid compositions herein are stable under various storage conditions, including refrigerated and ambient conditions. As used herein, the term "stable" refers to the oral liquid composition retaining at least about 90% of the initial valsartan amount, retaining at least about 95% of the initial valsartan amount, or retaining at least about 98% of the initial valsartan amount at the end of a given storage period under specified storage conditions. The term "stable" can also refer to an oral liquid composition including about 1% w/w or less total impurities or related substances, about 0.5% w/w or less total impurities or related substances, or about 0.4% w/w or less total impurities or related substances at the end of a given storage period under specified storage conditions. The term "stable" can also refer to an oral liquid composition having about 0.5% w/w or less individual impurities or related substances, or 0.2% w/w or less individual impurities or related substances at the end of a given storage period under specified storage conditions. The term "stable" can also refer to an oral liquid composition having less than about $10^2$ total aerobic microbial count at the end of a given storage period under specified storage conditions. The term "stable" can also refer to an oral liquid composition having less than $10^1$ total combined yeast and mold count at the end of a given storage period under specified storage conditions. The term "stable" can also refer to the absence or non-detection of *Escherichia coli* and/or *Burkholderia cepacia* within the oral liquid composition following a given storage period under specified storage conditions.

In some embodiments, the oral liquid composition herein is stable under refrigerated (5° C.±3° C.), and ambient conditions (25° C.±2° C. and 40%±5% RH) for at least 12 weeks, at least 16 weeks, at least 20 weeks, at least 24 weeks, at least 28 weeks, at least 32 weeks, at least 36 weeks, at least 48 weeks, at least 52 weeks, at least 60 weeks, at least 72 weeks, at least 84 weeks, at least 96 weeks, at least 104 weeks, at least 108 weeks, or at least 120 weeks. In certain embodiments, the oral liquid composition herein is stable under refrigerated (5° C.±3° C.) and ambient conditions (25° C.±2° C. and 40%±5% RH) for up to 12 weeks, up to 16 weeks, up to 20 weeks, up to 24 weeks, up to 28 weeks, up to 32 weeks, up to 36 weeks, up to 48 weeks, up to 52 weeks, up to 60 weeks, up to 72 weeks, up to 84 weeks, up to 96 weeks, up to 104 weeks, up to 108 weeks or up to 120 weeks. Ambient conditions, also referred to as controlled room temperature (CRT) conditions, include temperature and/or relative humidity that are at ambient levels (e.g., 25° C.±2° C. and 40%±5% RH). In some instances, ambient conditions are at about 20° C., about 21° C., about 22° C., about 23° C., about 24° C., about 25° C., about 26° C., about 27° C., about 28° C., about 29° C., or about 30° C. In certain embodiments, ambient conditions include a range of temperatures, all at 40%±5% relative humidity, for example, from about 23° C. to about 27° C., about 22° C. to about 28° C., or about 24° C. to about 26° C. In certain embodiments, ambient conditions include a range of relative humidities, all at 25° C.±2° C., for example, from about 37% to about 42%, about 34% to about 47%, or about 36% to about 46% relative humidity. In other instances, an ambient condition is about 45% RH, about 50% RH, about 55% RH, about 60% RH, or about 65% RH. Refrigerated conditions include temperatures and/or relative humidity in typical refrigeration units (e.g., 5±3° C.). In certain embodiments, refrigerated conditions include a range of temperatures, for example, from about 1° C. to about 10° C., about 2° C. to about 9° C., about 3° C. to about 8° C., or about 1° C. to about 8° C. In some instances, refrigerated conditions are at about 2° C., about 3° C., about 4° C., about 5° C., about 6° C., about 7° C., or about 8° C.

In further embodiments, the stable oral liquid composition disclosed herein, stored under ambient or refrigerated conditions for a specified storage period, provides similar, consistent, or equivalent pharmacokinetic parameters as an oral liquid composition that is formulated immediately prior to administration to a subject (i.e., freshly made). In other words, the oral liquid composition disclosed herein exhibits high stability after a specified storage period to provide similar, consistent, or equivalent pharmacokinetic parameters as a freshly made oral liquid composition. For example, a 104-week stable oral liquid composition, stored under controlled room temperature conditions, provides pharmacokinetic parameters similar, consistent, or equivalent to an oral liquid composition made five minutes prior to administration. Pharmacokinetic parameters for valsartan include $C_{max}$, $T_{max}$, $AUC_{last}$, $AUC_{inf}$, $T_{1/2}$, and $C_{last}$.

In some instances, administration of an oral liquid composition herein provides one or more pharmacokinetic parameters within 80% to 125%, 80% to 120%, 85% to 125%, 90% to 110% of the same parameter(s) obtained from administration of a freshly made liquid composition after the oral liquid composition herein has been stored at ambient conditions of 25° C.±2° C. and 40%±5% relative humidity for up to 12 weeks, up to 16 weeks, up to 20 weeks, up to 24 weeks, up to 28 week, up to 32 weeks, up to 36 weeks, up to 48 weeks, up to 52 weeks, up to 60 weeks, up to 72 weeks, up to 84 weeks, up to 96 weeks, up to 104 weeks, up to 108 weeks or at least 120 weeks, after preparation.

Methods of Treatment:

In another aspect, methods of treatment comprising administering an oral liquid composition disclosed herein to a subject in need thereof are provided are. In some embodiments, an oral liquid composition herein can be used to treat hypertension in a subject. Hypertension, as used herein, includes both primary (essential) hypertension or secondary hypertension. Hypertension can be classified in cases when blood pressure values are greater than or equal to 140/90 (systolic/diastolic) mm Hg in an adult subject. In other embodiments, the oral liquid composition disclosed herein treats primary (essential) hypertension in a subject. In yet other embodiments, the oral liquid composition herein treats secondary hypertension in a subject. In certain embodiments, the subject is a pediatric subject. Pediatric hypertension can be classified in cases where the child's blood pressure is greater than the 95th percentile for the patient's age, sex and height. In some embodiments, the subject is a geriatric subject. Hypertension in geriatric patients is defined similarly to that in adult patients, i.e., blood pressure values greater than or equal to 140/90 (systolic/diastolic) mm Hg.

In some embodiments, the oral liquid compositions herein can be used to treat heart failure. In certain embodiments, the oral liquid compositions herein can be used to reduce cardiovascular mortality in clinically stable patients with left ventricular failure or left ventricular dysfunction following myocardial infarction.

Dosing:

In one aspect, the oral liquid compositions herein are used for the treatment of diseases and conditions disclosed herein. In addition, a method for treating any of the diseases or conditions disclosed herein for a subject in need of such treatment involves administration of therapeutically effective amounts of the oral liquid compositions herein to the subject.

Dosages of the oral liquid compositions disclosed herein can be determined by any suitable method. Maximum tolerated dose (MTD) and maximum response dose (MRD) for valsartan can be determined via established animal and human experimental protocols. For example, toxicity and therapeutic efficacy of valsartan can be determined by standard pharmaceutical procedures in cell cultures or experimental animals, including, but not limited to, determination of the $LD_{50}$ (the dose lethal to 50% of the population) and the $ED_{50}$ (the dose therapeutically effective in 50% of the population). The dose ratio between the toxic and therapeutic effects is known as the therapeutic index, and it can be expressed as a ratio between $LD_{50}$ and $ED_{50}$. Valsartan dosages exhibiting high therapeutic indices are desirable. The data obtained from cell culture assays and animal studies can be used in formulating a range of dosage for use in humans. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximal response or of maximum tolerated dose, are readily obtained via these protocols.

In some embodiments, the dose of valsartan for treating adult hypertension in the oral liquid composition is about 80 mg or about 160 mg once daily. In certain embodiments, valsartan can be administered over a dose range of 80 mg to 320 mg daily, administered once a day for treating adult hypertension. In various embodiments, valsartan in the oral liquid composition can be administered over a dose range from about 70 mg to about 170 mg, about 75 mg to about 165 mg, about 85 mg to about 155 mg, about 90 mg to about 150 mg, about 95 mg to about 140 mg, about 70 mg to about 330 mg, about 90 mg to about 300 mg, about 100 mg to about 280 mg, about 120 mg to about 250 mg, about 70 mg to about 325 mg, or about 85 mg to about 310 mg daily, administered once a day for treating adult hypertension.

In some embodiments, the dose of valsartan for treating pediatric hypertension in the oral liquid composition is about 1.3 mg/kg once daily, up to about 40 mg total. In other embodiments, valsartan in the oral liquid composition can be administered over a dose range of about 1.3 to about 2.7 mg/kg once daily, up to about 40 mg to about 160 mg total for treating pediatric hypertension. In certain embodiments, valsartan in the oral liquid composition can be administered over a dose range of about 1.1 to about 2.8 mg/kg, about 1.5 mg/kg to about 2.5 mg/kg or about 1.7 to about 2.2 mg/kg once daily. In certain embodiments valsartan can be administered over a range of about 30 mg to about 170 mg, about 50 mg to about 150 mg, 70 mg to about 130 mg, 80 mg to about 120 mg, 90 mg to about 110 mg, or 45 mg to about 155 mg total daily, for treating pediatric hypertension.

In other embodiments, the dose of valsartan in the oral liquid composition for treating heart failure is about 40 mg twice daily. In yet other embodiments, valsartan in the oral liquid composition can be administered over a dose range of about 40 mg to about 160 mg twice daily for treating heart failure. In certain embodiments, valsartan can be administered over a dose range of about 30 mg to about 170 mg, about 50 mg to about 150 mg, 70 mg to about 130 mg, 80 mg to about 120 mg, 90 mg to about 110 mg, or 45 mg to about 155 mg twice daily for treating heart failure.

In other embodiments, the dose of valsartan in the oral liquid composition for reducing cardiovascular mortality in clinically stable patients with left ventricular failure or left ventricular dysfunction following myocardial infarction is about 20 mg twice daily. In other embodiments, valsartan in the oral liquid composition can be administered over a dose range of about 20 mg to about 160 mg twice daily for reducing cardiovascular mortality in clinically stable patients with left ventricular failure or left ventricular dysfunction following myocardial infarction. In certain embodiments, valsartan in the oral liquid composition can be administered over a dose range of about 10 mg to about 170 mg, about 35 mg to about 140 mg, about 50 mg to about 130 mg, about 60 mg to about 110 mg, about 70 mg to about 100 mg, about 25 mg to about 155 mg, or about 30 mg to about 145 mg, twice daily for reducing cardiovascular mortality in clinically stable patients with left ventricular failure or left ventricular dysfunction following myocardial infarction.

In some embodiments, the oral liquid composition is provided for administration to a human subject at a maximum tolerated dose (MTD) of valsartan. In certain embodiments, the amount of valsartan in the oral liquid composition administered to a human subject is from about 10% to about 90% of the MTD, from about 25% to about 75% of the MTD, or about 50% of the MTD. In certain embodiments, the amount of the oral liquid composition administered to a human subject ranges from about 20% to about 80% of the MTD, about 30% to about 70% of the MTD, about 40% to about 60% of the MTD, or about 20% to about 60% of the MTD. In certain other embodiments, the amount of the oral liquid composition administered is at least about 5%, 10%, 15%, 20%, 25%, 30%, 35%, 40%, 45%, 50%, 55%, 60%, 65%, 70%, 75%, 80%, 85%, 90%, 95%, 99%, or higher, or any range derivable therein, of the MTD for valsartan.

In some embodiments, the oral liquid composition is provided in a dosage that is similar, comparable, or equivalent to a dosage of a known valsartan tablet formulation. In other embodiments, the oral liquid composition is provided in a dosage that provides similar, comparable, or equivalent pharmacokinetic parameters (e.g., AUC, $C_{max}$, $T_{max}$, $C_{min}$, $T_{1/2}$) as a dosage of a commercially available valsartan tablet formulation. Similar, comparable, or equivalent pharmacokinetic parameters, in some instances, refer to within 80% to 125%, 80% to 120%, 85% to 125%, 90% to 110%, or increments therein, of the given values. It should be recognized that the ranges can, but need not be, symmetrical, e.g., 85% to 105%.

The term "AUC" as used herein refers to the integral of the concentration-time curve. The terms "$AUC_{last}$" and "$AUC_{0 \to t}$" as used herein refer to the area under a plasma concentration versus time curve from time 0 to the time of the last measured concentration of drug within the plasma. The terms "$AUC_{inf}$" and "$AUC_{0 \to \infty}$" as used herein refer to the area under a plasma concentration versus time curve from time 0 to infinity.

Certain non-limiting embodiments of the oral liquid composition of the present disclosure include administration of an oral liquid composition including 80 mL of valsartan (4 mg/mL, a total of 320 mg valsartan) wherein the composition results in a valsartan $AUC_{last}$ ranging from about 33,878 ng*h/mL to about 70,475 ng*h/mL. More generally, certain non-limiting embodiments of administration of 80 mL of the oral liquid composition including 4 mg/mL valsartan (total of 320 mg valsartan) result in a valsartan $AUC_{last}$ ranging from about 25,000 ng*h/mL to about 78,000 ng*h/mL, or has any $AUC_{last}$ value or falls within any $AUC_{last}$ range subsumed therein, such as, for example, about 26,000 ng*h/mL to about 77,000 ng*h/mL, about 27,000 ng*h/mL to about 76,000 ng*h/mL, about 28,000 ng*h/mL to about 75,000 ng*h/mL, about 29,000 ng*h/mL to about 74,000 ng*h/mL, about 30,000 ng*h/mL to about 73,000 ng*h/mL, about 31,500 ng*h/mL to about 72,500 ng*h/mL, about 32,000 ng*h/mL to about 72,000 ng*h/mL, about 32,500 ng*h/mL to about 71,500 ng*h/mL, about 33,000 ng*h/mL to about 71,000 ng*h/mL, about 33,500 ng*h/mL to about 70,500 ng*h/mL, about 34,000 ng*h/mL to about 70,000 ng*h/mL, about 34,500 ng*h/mL to about 69,500 ng*h/mL, about 35,000 ng*h/mL to about 69,000 ng*h/mL, about 37,500 ng*h/mL to about 68,000 ng*h/mL, or about 38,000 ng*h/mL to about 67,000 ng*h/mL.

Certain non-limiting embodiments of the oral liquid composition of the present disclosure include administration of an oral liquid composition including 80 mL of valsartan (4 mg/mL, a total of 320 mg valsartan) wherein the composition results in a valsartan $AUC_{inf}$ ranging from about 35,162 ng*h/mL to about 72,130 ng*h/mL. More generally, certain non-limiting embodiments of administration of 80 mL of the oral liquid composition including 4 mg/mL valsartan (total of 320 mg valsartan) result in a valsartan $AUC_{inf}$ ranging from about 30,000 ng*h/mL to about 78,000 ng*h/mL, or has any $AUC_{inf}$ value or falls within any $AUC_{inf}$ range subsumed therein, such as, for example, about 32,500 ng*h/mL to about 77,000 ng*h/mL, about 33,000 ng*h/mL to about 76,000 ng*h/mL, about 33,500 ng*h/mL to about 75,500 ng*h/mL, about 34,000 ng*h/mL to about 75,000 ng*h/mL, about 34,500 ng*h/mL to about 77,000 ng*h/mL, about 34,750 ng*h/mL to about 76,000 ng*h/mL, about 35,000 ng*h/mL to about 75,000 ng*h/mL, about 36,000 ng*h/mL to about 74,000 ng*h/mL, about 37,000 ng*h/mL to about 73,000 ng*h/mL, about 38,000 ng*h/mL to about 72,000 ng*h/mL, about 39,000 ng*h/mL to about 71,000 ng*h/mL, about 40,000 ng*h/mL to about 70,000 ng*h/mL, about 45,000 ng*h/mL to about 76,000 ng*h/mL, about 50,000 ng*h/mL to about 76,500 ng*h/mL, about 55,000 ng*h/mL to about 77,000 ng*h/mL, about 60,000 ng*h/mL to about 76,000 ng*h/mL, or about 65,000 ng*h/mL to about 76,500 ng*h/mL.

The pharmacokinetic parameter $C_{max}$ refers to the maximum (i.e., peak) serum concentration of a specific compound in the body of a subject after a pharmaceutical composition or compound has been administered to the subject. The term "$C_{last}$" as used herein refers to the last observed quantifiable concentration of a specific compound in the body of a subject after a pharmaceutical composition or compound has been administered to the subject.

One non-limiting embodiment herein is directed to administration of an oral liquid composition including 80 mL of valsartan (4 mg/mL, a total of 320 mg valsartan) wherein the composition results in a valsartan $C_{max}$ ranging from about 8,281 ng/mL to 14,714 ng/mL in the subject following administration of the oral liquid composition. In certain non-limiting embodiments, the valsartan $C_{max}$ achieved following oral administration of the oral liquid composition to a subject is within the range of from about 7,500 ng/mL to about 16,000 ng/mL, or has any $C_{max}$ value or falls within any $C_{max}$ range subsumed therein, such as, for example, from about 7,700 ng/mL to about 17,000 ng/mL, about 7,800 ng/mL to about 16,500 ng/mL, about 7,850 ng/mL to about 16,250 ng/mL, about 7,900 ng/mL to about 16,000 ng/mL, about 8,000 ng/mL to about 15,500 ng/mL, about 8,100 ng/mL to about 15,000 ng/mL, about 8,150 ng/mL to about 14,900 ng/mL, about 8,200 ng/mL to about 14,800 ng/mL, about 8,250 ng/mL to about 14,750 ng/mL, about 8,300 ng/mL to about 14,725 ng/mL, about 8,400 ng/mL to about 14,700 ng/mL, about 8,500 ng/mL to about 14,600 ng/mL, or about 8,900 ng/mL to about 14,500 ng/mL.

The pharmacokinetic parameter $T_{max}$ for a pharmaceutical composition or compound is the time after administration to a subject at which the $C_{max}$ is observed in the subject. As such, the term "$T_{max}$" as used herein refers to the time after administration of a drug when the maximum plasma concentration is reached.

One non-limiting embodiment herein is directed to administration of an oral liquid composition including 80 mL of valsartan (4 mg/mL, a total of 320 mg valsartan) to a subject, wherein the composition results in a valsartan $T_{max}$ of about 0.66 h to about 2.66 h in the subject. In various non-limiting embodiments, following the administration of the oral liquid composition including 80 mL of valsartan (4 mg/mL, a total of 320 mg valsartan) to a subject, the observed valsartan $T_{max}$ falls within the range from about 0.50 h to about 3.3 h, or has any $T_{max}$ value or falls within any $T_{max}$ range subsumed therein, such as, for example, from about 0.55 h to about 3.2 h, about 0.60 h to about 3.1 h, about 0.65 h to about 3.0 h, about 0.70 h to about 2.9 h, about 0.75 h to about 2.8 h, about 0.80 h to about 2.7 h, about 0.85 h to about 2.6 h, about 0.90 h to about 2.5 h, about 1.0 h to about 2.4 h, about 1.1 h to about 2.3 h, about 1.2 h to about 2.2 h, about 1.3 h to about 2.1 h, about 0.50 h to about 2.0 h, about 0.50 h to about 1.0 h, or about 0.4 h to about 2.25 h.

The term "absorptivity factor" as used herein refers to the maximum (i.e., peak) serum concentration of a specific compound in the body of a subject after a pharmaceutical composition or compound has been administered to the subject ($C_{max}$) divided by the area under the drug concentration-time curve from time 0 to infinity ($AUC_{inf}$).

Certain non-limiting embodiments according to the present disclosure include administration of an oral liquid composition including 80 mL of valsartan (4 mg/mL, a total of 320 mg valsartan) to a subject, wherein the composition results in an absorptivity factor for valsartan ranging from about 0.040 $h^{-1}$ to about 0.388 $h^{-1}$ in the subject. In certain non-limiting embodiments, the absorptivity factor for valsartan resulting following administration of an oral liquid composition including 80 mL of valsartan (4 mg/mL, a total of 320 mg valsartan) to a subject is in a range of from about 0.01 $h^{-1}$ to 1.0 $h^{-1}$, or has any value or falls within any range subsumed therein, such as, for example, from about 0.015 $h^{-1}$ to about 0.90 $h^{-1}$, from about 0.02 $h^{-1}$ to about 0.80 $h^{-1}$, from about 0.025 $h^{-1}$ to about 0.70 $h^{-1}$, from about 0.03 $h^{-1}$ to about 0.60 $h^{-1}$, from about 0.035 $h^{-1}$ to about 0.55 $h^{-1}$, from about 0.04 $h^{-1}$ to about 0.50 $h^{-1}$, from about 0.045 $h^{-1}$ to about 0.45 $h^{-1}$, from about 0.05 $h^{-1}$ to about 0.40 $h^{-1}$, from about 0.07 $h^{-1}$ to about 0.35 $h^{-1}$, from about 0.09 $h^{-1}$ to about 0.30 $h^{-1}$, from about 0.1 $h^{-1}$ to about 0.25 $h^{-1}$, from about 0.20 $h^{-1}$ to about 0.50 $h^{-1}$, from about 0.30 $h^{-1}$ to about 0.80 $h^{-1}$, or from about 0.050 $h^{-1}$ to about 0.50 $h^{-1}$.

Administration:

The oral liquid compositions described herein can be administered at a dosage disclosed herein or at other appropriate dose levels contemplated by a medical practitioner. In certain embodiments, the oral liquid compositions disclosed herein are administered for prophylactic and/or therapeutic treatments. In certain therapeutic applications, the oral liquid compositions are administered to a patient already suffering from an indication, e.g., hypertension, in a therapeutically effective amount sufficient to cure the disease or at least partially arrest or ameliorate the symptoms, e.g., lower blood pressure. Amounts effective for this use depend on, for example, the age of the patient, severity of the disease, previous therapy, the patient's health status, weight, and response to the oral liquid compositions, and are within the judgment of the treating physician. Therapeutically effective amounts are optionally determined by methods including, but not limited to, a dose escalation clinical trial.

In certain embodiments wherein the patient's condition does not improve, upon the doctor's discretion, the oral liquid composition disclosed herein may be administered chronically, that is, for an extended period of time, including throughout the duration of the patient's life to ameliorate or otherwise control or limit the symptoms of the patient's disease. In some embodiments, administration of the oral liquid composition continues until complete or partial response of a disease occurs.

In some embodiments, an oral liquid composition herein is administered to a subject who is in a fasted state. A fasted state refers to the state of a subject who has gone without food or fasted for a specified amount of time. General fasting periods include at least 4 hours, at least 6 hours, at least 8 hours, at least 10 hours, at least 12 hours, at least 14 hours, and at least 16 hours without food. In certain embodiments, an oral liquid composition herein is administered to a subject who has fasted overnight.

In some embodiments, an oral liquid composition herein is administered to a subject who is in a fed state. A fed state refers to the state of a subject who has taken food or has had a meal. In certain embodiments, an oral liquid composition is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, 2 hours post-meal, or more. In certain instances, an oral liquid composition is administered to a subject along with food.

Further Combinations:

In some embodiments, the treatment of certain diseases or conditions (e.g., hypertension, treatment of heart failure and reduction of cardiovascular mortality in clinically stable patients with left ventricular failure or left ventricular dysfunction following myocardial infarction) in a subject with the oral liquid compositions disclosed herein encompasses additional therapies and treatment regimens with other active pharmaceutical ingredients. In some embodiments, additional therapies and treatment regimens can include sequential or concurrent administration of a second active ingredient to a subject to treat the same or different disease or condition being treated with the oral liquid composition. In various embodiments, additional therapies and treatment regimens include sequential or concurrent administration of a second active ingredient to a subject to treat adjunct conditions associated with the disease or condition or a side effect from the oral liquid composition in the therapy.

Possible additional active ingredients for use in combination with an oral liquid composition as disclosed herein, include, but are not limited to, diuretics (loop, thiazide, potassium-sparing, and the like), beta blockers (metoprolol, propanolol, pronethalol, and the like), alpha blockers (phentolamine, phenoxybenzamine, tamsulosin, prazosin, and the like), mixed alpha and beta blockers (bucindolol, carvedilol, labetalol), calcium channel blockers (dilitazem, verapamil, dihydropyridines such as nifedipine, amlodipine, etc., and the like), angiotensin II receptor antagonists (saralasin, losartan, eprosartin, irbesartan, and the like), other ACE inhibitors (lisinopril, captopril, quinapril, ramipril, zofenopril, and the like), aldosterone antagonists (eplerenone, spironolactone and the like), vasodilators (hydralazine and the like), and alpha-2 agonists (clonidine, moxonidine, guanabenz and the like).

EXAMPLES

Example 1. Preparation of Three Oral Liquid Compositions Including Valsartan

Three oral liquid compositions were prepared using the method described below. The following process describes the preparation of compositions #1, #3, and #4, the compositions of which are shown in Table 1 below.

TABLE 1

Compositions of oral liquid compositions #1 #2, and #3, all three oral liquid compositions including, by weight, 0.4% valsartan (4 mg/mL).

| Ingredient | Function | #1 % w/v | #3 % w/v | #4 % w/v | #1 mg/mL | #3 mg/mL | #4 mg/mL |
|---|---|---|---|---|---|---|---|
| Valsartan | API | 0.4 | 0.4 | 0.4 | 4 | 4 | 4 |
| Citric acid, anhydrous | Buffer | — | — | — | — | — | — |
| Potassium sorbate | Preservative | 0.2 | 0.2 | 0.1 | 2 | 2 | 1 |
| Grape Flavor | Flavor | 0.3 | 0.4 | 0.3 | 3 | 4 | 3 |
| Methylparaben | Preservative | 0.2 | 0.2 | 0.1 | 2 | 2 | 1 |
| Sodium citrate, dihydrate | Buffer | 1.2 | 1.2 | 1.0 | 12 | 12 | 10 |
| Sucralose | Sweetener | 0.01 | 0.02 | 0.02 | 0.1 | 0.2 | 0.2 |
| Poloxamer 188 | Solubilizer | 1.0 | 1.0 | 1.0 | 10 | 10 | 10 |
| Propylene Glycol | Solubilizer | 10.0 | 10.0 | 10.0 | 100 | 100 | 100 |
| Purified Water | Solvent | 86.69 | 86.58 | 87.08 | 866.9 | 865.8 | 870.8 |

Unless otherwise noted, all components were added in the quantities/concentrations provided in Table 1 and steps were performed at room temperature. Valsartan was mixed in propylene glycol with stirring until there were no visible valsartan particles in the mixture ("first mixture"). Methylparaben was added to the first mixture and stirred until there were no visible methylparaben particles in this second mixture.

In a separate vessel, poloxamer 188 was mixed in water and stirred until there were no visible poloxamer 188 particles in this third mixture. Sodium citrate dihydrate was then slowly added to the third mixture and stirred until there were no visible sodium citrate dihydrate particles in this fourth mixture.

The second mixture (valsartan, propylene glycol and methylparaben) was slowly added to the fourth mixture (poloxamer 188, water, and sodium citrate dihydrate) until the combined mixture was clear.

Potassium sorbate was added to the combined mixture and stirred until there were no visible potassium sorbate particles in this fifth mixture. Sucralose was then added to the fifth mixture and stirred until all particles were dissolved in this final mixture. For preparation of composition #1, water was added quantum satis up to 1000 g to the final mixture and then flavoring was added to form composition #1. For compositions #3 and #4, flavoring was added to the final mixture, and then water was added quantum satis up to 1000 g to form compositions #3 and #4.

Example 2. Preparation of an Oral Liquid Composition Including Valsartan

An oral liquid composition was prepared using the method described below. The following process describes the preparation of composition #2, the composition of which is shown in Table 2 below.

TABLE 2

Oral Liquid Composition #2, including by weight, 0.4% valsartan (4 mg/mL).

| Ingredient | Function | #2 % w/v | #2 mg/mL |
|---|---|---|---|
| Valsartan | API | 0.4 | 4 |
| Citric acid, anhydrous | Buffer | 0.2 | 2 |
| Potassium sorbate | Preservative | 0.2 | 2 |
| Grape Flavor | Flavor | 0.3 | 3 |
| Methylparaben | Preservative | 0.2 | 2 |
| Sodium citrate, dihydrate | Buffer | 1.2 | 12 |
| Sucralose | Sweetener | 0.03 | 0.3 |
| Poloxamer 188 | Solubilizer | 1.0 | 10 |
| Propylene Glycol | Solubilizer | 10.0 | 100 |
| Purified Water | Solvent | 86.47 | 864.7 |

Unless otherwise noted, all components were added in the quantities/concentrations provided in Table 2 and all steps were performed at room temperature. Valsartan was mixed in propylene glycol with stirring until there were no visible valsartan particles in the (first) mixture. Methylparaben was then added to the first mixture and stirred until there were no visible methylparaben particles in this second mixture.

In a separate vessel, poloxamer 188 was mixed in water and stirred until there were no visible poloxamer 188 particles in this third mixture. Sodium citrate dihydrate was then slowly added to the third mixture and stirred until there were no visible sodium citrate dihydrate particles in this fourth mixture. Citric acid anhydrous was then added to the fourth mixture with stirring until there were no visible citric acid anhydrous particles in this fifth mixture.

The second mixture (valsartan, propylene glycol and methylparaben) was slowly added to the fifth mixture (poloxamer 188, water, sodium citrate dihydrate and citric acid anhydrous) with stirring until the combined mixture was clear.

Potassium sorbate was added to the combined mixture and stirred until there were no visible potassium sorbate particles in this sixth mixture. Sucralose was then added to the sixth mixture and stirred until all particles were dissolved in this final mixture. Flavoring was added to the final mixture, and then water was added quantum satis up to 1000 g to form composition #2.

Example 3. Preparation of an Oral Liquid Composition Including 0.4%, by Weight, (4 mg/mL) Valsartan An oral liquid composition including valsartan was prepared using the method described below. The following process describes the preparation of composition #5, the composition of which is shown in Table 3 below.

TABLE 3

Oral Liquid Composition #5, including by weight, 0.4% valsartan (4 mg/mL).

| Ingredient | Function | #5 % w/v | #5 mg/mL |
|---|---|---|---|
| Valsartan | API | 0.4 | 4 |
| Citric acid, anhydrous | Buffer | — | — |
| Potassium sorbate | Preservative | 0.2 | 2 |
| Grape Flavor | Flavor | 0.3 | 3 |
| Methylparaben | Preservative | 0.2 | 2 |
| Sodium citrate, dihydrate | Buffer | 1.0 | 10 |
| Sucralose | Sweetener | 0.02 | 0.2 |
| Poloxamer 188 | Solubilizer | 1.0 | 10 |
| Propylene Glycol | Solubilizer | 10.0 | 100 |
| Purified Water | Solvent | 86.88 | 868.8 |

Unless otherwise noted, all components were added in the quantities/concentrations provided in Table 3 and all steps were performed at room temperature. Propylene glycol was added to a reaction vessel. Water was then added to the reaction vessel and the (first) mixture was stirred. Poloxamer 188 was added to the first mixture and stirred until there were no visible poloxamer 188 particles, forming a second mixture. Methylparaben was then added to the second mixture and stirred until there were no visible methylparaben particles, forming a third mixture. Sodium citrate dihydrate was then added to the third mixture and stirred until there were no visible sodium citrate dihydrate particles, forming a fourth mixture. Valsartan was slowly added to the fourth mixture and stirred until there were no visible valsartan particles, forming a fifth mixture. Potassium sorbate was then added to the fifth mixture and stirred until there were no potassium sorbate particles, forming a sixth mixture. Sucralose and grape flavor were added to the sixth mixture and stirred until there were no sucralose or grape flavor particles, forming a final mixture. Water was added to the final mixture, quantum satis to 1000 g and stirred.

Figure 1B:
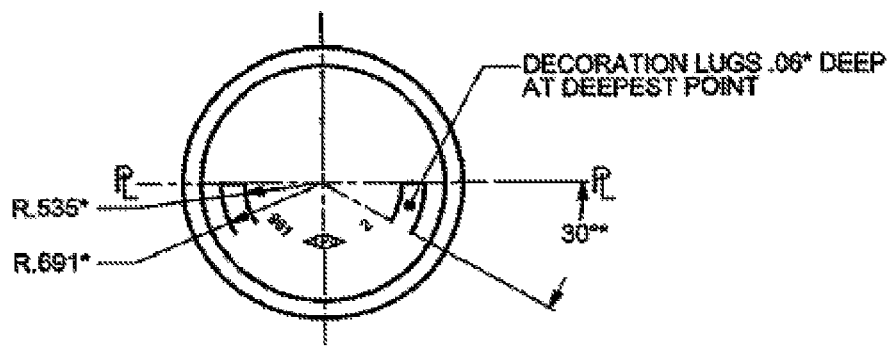
Figure 1C:
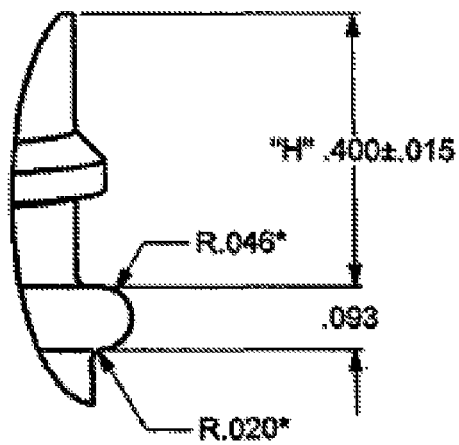
Figure 2A:
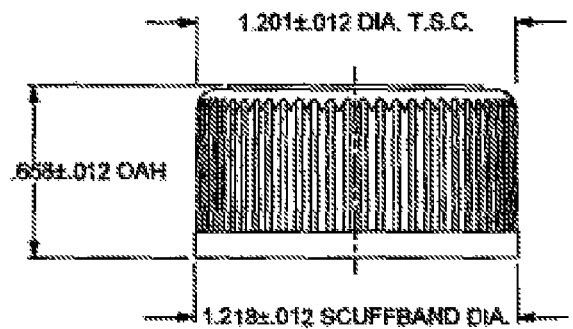
Figure 2B:
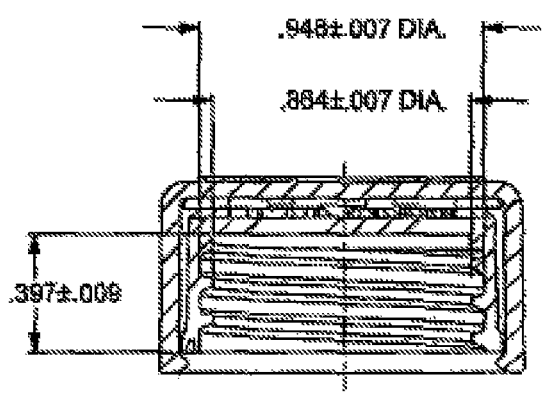

Example 4. Stability Study of the Oral Liquid Composition Including 0.4% Valsartan (4 mg/mL) Stored in a Container Closure System Including 4 Oz. High Density Polyethylene (HDPE) Bottles For purposes of conducting a stability study, 120 mL oral liquid composition #5 samples of Example 3 were packaged in a container closure system. For purposes of conducting a stability study, oral liquid composition #5 samples of Example 3 were packaged in a container closure system. Each container closure system, as shown in FIGS. 1A-1C, included a 4 ounce (120 mL), Boston round white (colorant: white 11078 AMPACET), High Density Polyethylene ("HDPE"), (resin: MARLEX HEIM 5502BN), bottle with a 24 mm SECURX™ ribbed side pictorial top (resin: INEOS H20E-00), white closure (colorant: white 11343 AMPACET), with a foam liner (liner: SELIG SEALING 0.035" C25 FSLE5-9) (see FIGS. 2A and 2B). Samples were stored upright under the following storage conditions: refrigerated conditions (REF) (5° C.±3° C.); controlled room temperature conditions (25° C.±2° C. and 40%±5% RH); intermediate conditions (INT) (35° C.±2° C. and 65%±5% RH); and accelerated conditions (ACC) (40° C.±2° C. and not more than (NMT) 25% RH). The samples were stored in a calibrated stability chamber. Samples of the oral liquid composition stored in the chamber were taken at set time intervals to assay for valsartan, pH, individual unspecified impurities, total impurities, total aerobic microbial count, and total yeast/mold count. Samples were analyzed using a High Performance Liquid Chromatography (HPLC) system equipped with a pump, autosampler, UV detector, and a suitable data acquisition system. The HPLC column used included packing L1 (C18), 5 μm, 250 mm×4.6 mm. The HPLC parameters used included 230 nm detection, a flow rate of 1.5 mL/min, an injection volume of 20 μL, at ambient temperature, for a run time of 25 minutes using a mobile phase of acetonitrile, DI water, and glacial acetic acid (40:60:0.1).

Table 4 reports the stability data for the oral liquid composition including, by weight, 0.4% valsartan (4 mg/mL), stored under refrigerated conditions (5° C.±3° C.) and in the 4 oz. HDPE bottles of the container closure system, at 3, 6, 9, 12, 18, and 24 month time intervals.

TABLE 4

Stability assay for the oral liquid composition containing, by weight, 0.4% valsartan, (4 mg/mL) tested under refrigerated conditions (5° C. ± 3° C.) and stored in 4 oz. HDPE bottles.

| Time | pH | Valsartan[1] (%) | Individual Unspecified Impurities (%) | Total Impurities (%) | Total Aerobic Microbial Count | Total Yeast/ Mold Count |
|---|---|---|---|---|---|---|
| Initial | 5.9 | 98.6 | <0.05 | <0.05 | <10 cfu[2]/g | <10 cfu/g |
| 3 mos. | 5.9 | 99.9 | <0.05 | <0.05 | NA[3] | NA |
| 6 mos. | 5.9 | 98.6 | <0.05 | <0.05 | NA | NA |
| 9 mos. | 5.9 | 101.1 | <0.05 | <0.05 | NA | NA |
| 12 mos. | 6.0 | 100.5 | <0.05 | <0.05 | NA | NA |
| 18 mos. | 6.0 | 99.1 | <0.05 | <0.05 | NA | NA |
| 24 mos. | 6.0 | 100.0 | <0.05 | <0.05 | <10 cfu/g | <10 cfu/g |

[1]Assayed percent valsartan present at specified time.
[2]cfu = colony forming units
[3]NA = not applicable As indicated in Table 4, the oral liquid composition #5 of Example 3, originally including 0.4% valsartan (4 mg/mL), was stable for at least 24 months when stored under refrigerated (REF) conditions in the 4 oz. HDPE bottles of the container closure system. The stability assay showed that 100.0% of the original valsartan was retained in the oral liquid composition over the course of the refrigerated stability conditions assay for 24 months.

Table 5 reports the stability data for the oral liquid composition #5, originally containing 0.4% valsartan (4 mg/mL), stored under standard conditions (25° C.±2° C. and 40%±5% RH) in 4 oz. HDPE bottles of the container closure system, at 3, 6, 9, 12, 18, and 24 month time intervals.

TABLE 5

Stability assay for oral liquid composition #5 tested under standard conditions (25° C. ± 2° C. and 40% ± 5% RH) and stored in 4 oz. HDPE bottles.

| Time | pH | Valsartan[1] (%) | Individual Unspecified Impurities (%) | Total Impurities (%) | Total Aerobic Microbial Count | Total Yeast/ Mold Count |
|---|---|---|---|---|---|---|
| Initial | 5.9 | 98.6 | <0.05 | <0.05 | <10 cfu[2]/g | <10 cfu/g |
| 3 mos. | 5.9 | 99.1 | <0.05 | <0.05 | NA[3] | NA |
| 6 mos. | 5.9 | 98.7 | <0.05 | <0.05 | NA | NA |
| 9 mos. | 6.0 | 100.9 | 0.05 | 0.1 | NA | NA |
| 12 mos. | 6.0 | 100.8 | 0.05 | 0.1 | <10 cfu/g | <10 cfu/g |
| 18 mos. | 6.0 | 99.6 | <0.05 | <0.05 | NA | NA |
| 24 mos. | 6.0 | 99.6 | 0.1 | 0.1 | <10 cfu/g | <10 cfu/g |

[1]Assayed percent valsartan present at specified time.
[2]cfu = colony forming units
[3]NA = not applicable As indicated in Table 5, the oral liquid composition #5, initially including 0.4% valsartan (4 mg/mL), was stable for at least 24 months when stored under standard conditions of 25° C.±2° C. and 40%±5% relative humidity. The stability assay showed 99.6% of the original valsartan was retained in the oral liquid composition over the course of the standard stability conditions assay for 24 months and stored in 4 oz. HDPE bottles of the container closure system.

Table 6 reports the stability data for the oral liquid composition #5, originally containing 0.4% valsartan (4 mg/mL), tested under intermediate conditions (35° C.±2° C. and 65%±5% RH) in 4 oz. HDPE bottles of the container closure system, at 3, 6, 9, 12, 18, and 24 month time intervals.

TABLE 6

Stability assay for oral liquid composition #5 tested under intermediate conditions (35° C. ± 2° C. and 65% ± 5% RH) and stored in 4 oz. HDPE bottles.

| Time | pH | Valsartan[1] (%) | Individual Unspecified Impurities (%) | Total Impurities (%) | Total Aerobic Microbial Count | Total Yeast/ Mold Count |
|---|---|---|---|---|---|---|
| Initial | 5.9 | 98.6 | <0.05 | <0.05 | <10 cfu[2]/g | <10 cfu/g |
| 3 mos. | 5.9 | 99.5 | <0.05 | <0.05 | NA[3] | NA |
| 6 mos. | 5.9 | 100.1 | <0.05 | <0.05 | NA | NA |
| 9 mos. | 5.9 | 97.2 | <0.05 | <0.05 | NA | NA |
| 12 mos. | 5.9 | 99.2 | <0.05 | <0.05 | NA | NA |
| 18 mos. | 6.0 | 100.0 | 0.07 | 0.1 | NA | NA |
| 24 mos. | 6.0 | 99.2 | 0.08 | 0.1 | <10 cfu/g | <10 cfu/g |

[1]Assayed percent valsartan present at specified time.
[2]cfu = colony forming units
[3]NA = not applicable As indicated in Table 6, the oral liquid composition #5, originally including 0.4% valsartan (4 mg/mL), was stable for at least 24 months when stored under intermediate conditions of 35° C.±2° C. and 65%±5% relative humidity in 4 oz. HDPE bottles of the container closure system. The stability assay showed 99.2% of the original valsartan was retained in the oral liquid composition over the course of the intermediate stability conditions assay for 24 months.

Table 7 reports the stability data for the oral liquid composition #5, originally including 0.4% valsartan (4 mg/mL), tested under accelerated conditions (40° C.±2° C. and NMT 25% RH) in 4 oz. HDPE bottles of the container closure system, at 1, 2, 3, and 6 month time intervals.

TABLE 7

Stability assay for oral liquid composition #5 tested under accelerated conditions (40° C./2° C./NMT 25% RH) and stored in 4 oz. HDPE bottles.

| Time | pH | Valsartan[1] (%) | Individual Unspecified Impurities (%) | Total Impurities (%) | Total Aerobic Microbial Count | Total Yeast/ Mold Count |
|---|---|---|---|---|---|---|
| Initial | 5.9 | 98.6 | <0.05 | <0.05 | <10 cfu[2]/g | <10 cfu/g |
| 1 mos. | 5.9 | 99.5 | <0.05 | <0.05 | NA[3] | NA |
| 2 mos. | 6.0 | 99.7 | <0.05 | <0.05 | NA | NA |
| 3 mos. | 6.0 | 99.4 | <0.05 | <0.05 | NA | NA |
| 6 mos. | 5.9 | 99.1 | <0.05 | <0.05 | <10 cfu/g | <10 cfu/g |

[1]Assayed percent valsartan present at specified time.
[2]cfu = colony forming units
[3]NA = not applicable As indicated in Table 7, the oral liquid composition #5, originally including 0.4% valsartan (4 mg/mL), was stable for at least 6 months when stored under accelerated conditions of 40° C.±2° C. and NMT 25% relative humidity in 4 oz. HDPE bottles of the container closure system. The stability assay showed 99.1% of the original valsartan was retained in the oral liquid composition over the course of the accelerated stability conditions assay for 6 months.

Figure 3A:
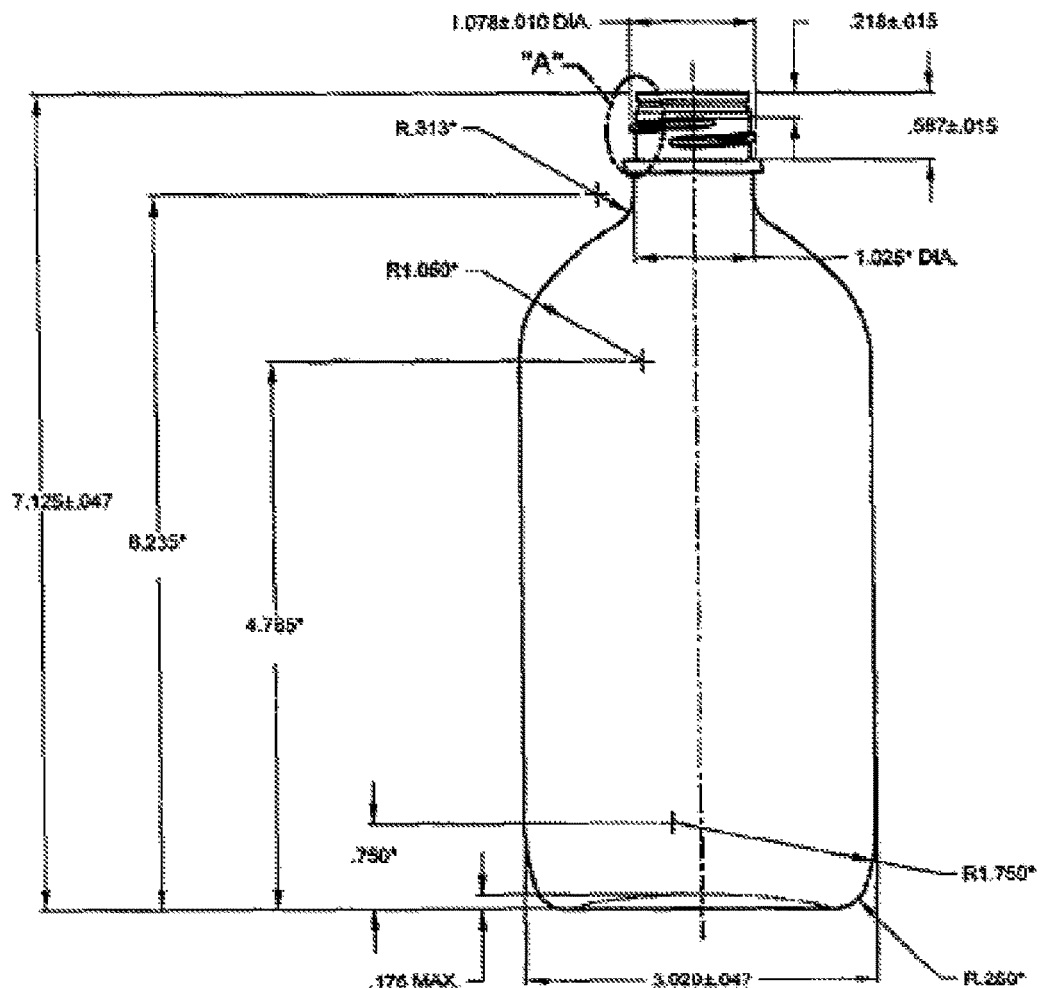
Figure 3B:
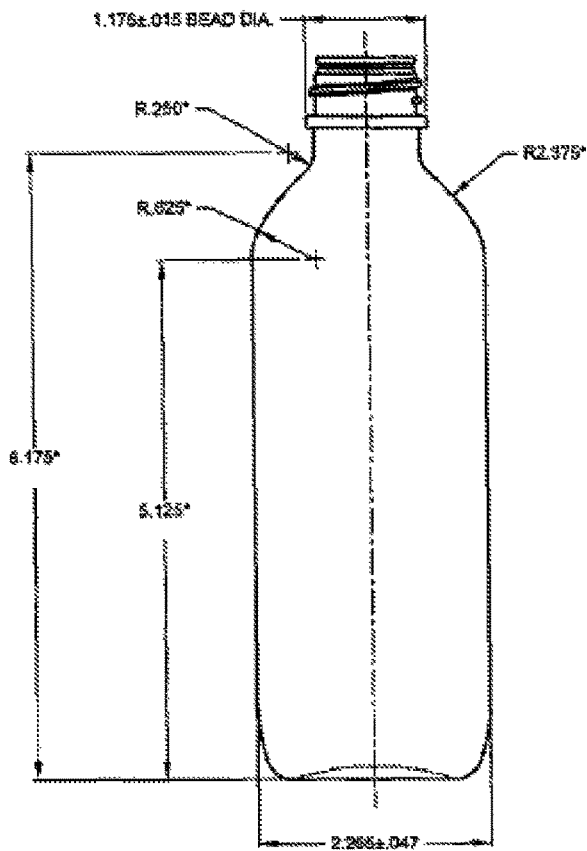
Figure 3C:
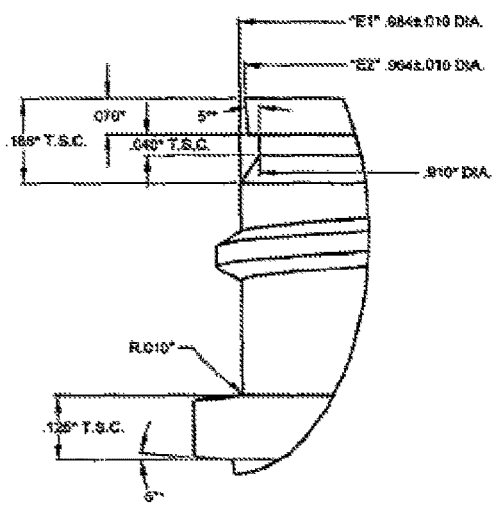
Figure 4A:
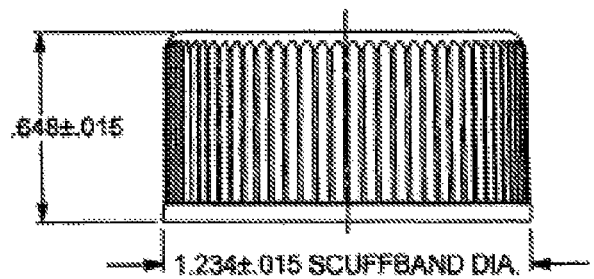
Figure 4B:
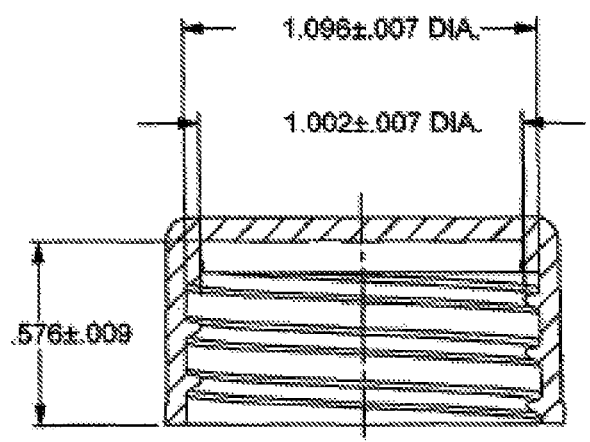

Example 5. Stability Study of the Oral Liquid Composition Including 0.4% Valsartan (4 mg/mL) Stored in a Container Closure System Including 16 Ounce (473 mL) High Density Polyethylene (HDPE) Bottles For purposes of conducting a stability study, the oral liquid composition #5 samples of Example 3, originally containing, by weight of the composition, 0.4% valsartan (4 mg/mL), were packaged in a container closure system and stored under specified conditions. Each container closure system, as shown in FIGS. 3A-3C, included a 16 ounce (473 mL), rectangular white (Colorant: White 11078 AMPACET), HDPE (Resin: MARLEX HEIM 5502BN) bottle with a 28/480 mm continuous thread ribbed side smooth top (Resin: INEOS H20E-00) white closure (Colorant: White 11343 AMPACET), with a foam liner (SELIG SEALING 0.035" C25 FSLE5-9), (see FIGS. 4A and 4B). Samples were stored upright under the following storage conditions: refrigerated conditions (REF) (5° C.±3° C.); controlled room temperature conditions (25° C.±2° C. and 40%±5% RH); intermediate conditions (INT) (35° C.±2° C./65%±5% RH); and accelerated conditions (ACC) (40° C.±2° C. and not more than (NMT) 25% RH). The stability samples were stored in a calibrated stability chamber. Samples of the stored oral liquid composition were taken at set time intervals to assay for valsartan, pH, individual unspecified impurities, total impurities, total aerobic microbial count, and total yeast/mold count. Samples were analyzed using a High Performance Liquid Chromatography (HPLC) system equipped with a pump, autosampler, UV detector, and a suitable data acquisition system. The HPLC column used included packing L1 (C18), 5 µm, 250 mm×4.6 mm. The HPLC parameters used included 230 nm detection, a flow rate of 1.5 mL/min, an injection volume of 20 µL, at ambient temperature, for a run time of 25 minutes using a mobile phase of acetonitrile, DI water, and glacial acetic acid (40:60:0.1).

Table 8 reports the stability data for the oral liquid composition #5 containing, by weight, 0.4% valsartan (4 mg/mL), tested under refrigerated conditions (5° C.±3° C.) stored in 16 oz. HDPE bottles of the container closure system, at 3, 6, 9, 12, 18, and 24 month time intervals.

TABLE 8

Stability assay for oral liquid composition #5 tested under refrigerated conditions (5° C. ± 3° C.) and stored in 16 oz. HDPE bottles.

| Time | pH | Valsartan[1] (%) | Individual Unspecified Impurities (%) | Total Impurities (%) | Total Aerobic Microbial Count | Total Yeast/ Mold Count |
|---|---|---|---|---|---|---|
| Initial | 5.9 | 99.4 | <0.05 | <0.05 | <10 cfu[2]/g | <10 cfu/g |
| 3 mos. | 5.9 | 99.1 | <0.05 | <0.05 | NA[3] | NA |
| 6 mos. | 5.9 | 99.5 | <0.05 | <0.05 | NA | NA |
| 9 mos. | 5.9 | 99.6 | <0.05 | <0.05 | NA | NA |
| 12 mos. | 6.0 | 100.1 | <0.05 | <0.05 | NA | NA |
| 18 mos. | 6.0 | 98.9 | <0.05 | <0.05 | NA | NA |
| 24 mos. | 6.0 | 99.8 | <0.05 | <0.05 | <10 cfu/g | <10 cfu/g |

[1]Assayed percent valsartan present at specified time.
[2]cfu = colony forming units
[3]NA = not applicable As shown in Table 8 above, the oral liquid composition #5, which originally included 0.4% valsartan (4 mg/mL), was stable for at least 24 months when stored under refrigerated conditions (5° C.±3° C.) in 16 oz. HDPE bottles of the container closure system. The stability assay showed 99.8% of the original valsartan was retained in the oral liquid composition over the course of the refrigerated stability conditions assay for 24 months while stored in 16 oz. HDPE bottles of the container closure system.

Table 9 reports the stability data for the oral liquid composition #5 containing, by weight, 0.4% valsartan (4 mg/mL), stored under standard conditions (25° C.±3° C. and 40%±5% RH) in 16 oz. HDPE bottles of the container closure system, at 3, 6, 9, 12, 18, and 24 month time intervals.

TABLE 9

Stability assay for oral liquid composition #5 tested under standard conditions (25° C. ± 2° C./40% ± 5% RH) and stored in 16 oz. HDPE bottles.

| Time | pH | Valsartan[1] (%) | Individual Unspecified Impurities (%) | Total Impurities (%) | Total Aerobic Microbial Count | Total Yeast/ Mold Count |
|---|---|---|---|---|---|---|
| Initial | 5.9 | 99.4 | <0.05 | <0.05 | <10 cfu[2]/g | <10 cfu/g |
| 3 mos. | 5.9 | 99.5 | <0.05 | <0.05 | NA[3] | NA |
| 6 mos. | 5.9 | 99.4 | <0.05 | <0.05 | NA | NA |
| 9 mos. | 6.0 | 99.7 | <0.05 | <0.05 | NA | NA |
| 12 mos. | 6.0 | 99.7 | 0.05 | 0.1 | <10 cfu/g | <10 cfu/g |
| 18 mos. | 6.0 | 99.0 | <0.05 | <0.05 | NA | NA |
| 24 mos. | 6.0 | 100.4 | 0.11 | 0.1 | <10 cfu/g | <10 cfu/g |

[1]Assayed percent valsartan present at specified time.
[2]cfu = colony forming units
[3]NA = not applicable As indicated in Table 9, the oral liquid composition #5, of Example 3, originally including, by weight, 0.4% valsartan (4 mg/mL), was stable for at least 24 months when stored under standard conditions of 25° C.±2° C. and 40%±5% relative humidity in 16 oz. HDPE bottles of the container closure system. The stability assay showed 100% of the original valsartan was retained in the oral liquid composition over the course of the standard stability conditions assay for 24 months while stored in 16 oz. HDPE bottles of the container closure system.

Table 10 reports the stability data for the oral liquid composition #5 including, by weight, 0.4% valsartan (4 mg/mL), stored under intermediate conditions (35° C.±2° C. and 65%±5% RH) in 16 oz. HDPE bottles of the container closure system, at 3, 6, 9, 12, 18, and 24 month time intervals.

TABLE 10

Stability assay for oral liquid composition #5 tested under intermediate conditions (35° C. ± 2° C. and 65% ± 5% RH) and stored in 16 oz. HDPE bottles.

| Time | pH | Valsartan[1] (%) | Individual Unspecified Impurities (%) | Total Impurities (%) | Total Aerobic Microbial Count | Total Yeast/Mold Count |
|---|---|---|---|---|---|---|
| Initial | 5.9 | 99.4 | <0.05 | <0.05 | <10 cfu[2]/g | <10 cfu/g |
| 3 mos. | 5.9 | 99.5 | <0.05 | <0.05 | NA[3] | NA |
| 6 mos. | 5.9 | 98.5 | <0.05 | <0.05 | NA | NA |
| 9 mos. | 5.9 | 97.8 | <0.05 | <0.05 | NA | NA |
| 12 mos. | 5.9 | 99.0 | <0.05 | <0.05 | NA | NA |
| 18 mos. | 6.0 | 100.1 | 0.07 | 0.1 | NA | NA |
| 24 mos. | 6.0 | 99.3 | 0.09 | 0.1 | <10 cfu/g | <10 cfu/g |

[1]Assayed percent valsartan present at specified time.
[2]cfu = colony forming units
[3]NA = not applicable As indicated in Table 10, the oral liquid composition #5, which originally included 0.4% valsartan (4 mg/mL), was stable for at least 24 months when stored under intermediate conditions of 35° C.±2° C. and 65%±5% relative humidity in 16 oz. HDPE bottles of the container closure system. The stability assay showed 99.3% of the original valsartan was retained in the oral liquid composition over the course of the intermediate stability conditions assay for 24 months while stored in 16 oz. HDPE bottles of the container closure system.

Table 11 reports the stability data for the oral liquid composition #5 containing, by weight, 0.4% valsartan (4 mg/mL), stored under accelerated conditions (40° C.±2° C./NMT 25% RH) in 16 oz. HDPE bottles of the container closure system, at 1, 2, 3, and 6 month time intervals.

TABLE 11

Stability assay for oral liquid composition #5 tested under accelerated conditions (40° C. ± 2° C./NMT 25% RH) and stored in 16 oz. HDPE bottles.

| Time | pH | Valsartan[1] (%) | Individual Unspecified Impurities (%) | Total Impurities (%) | Total Aerobic Microbial Count | Total Yeast/Mold Count |
|---|---|---|---|---|---|---|
| Initial | 5.9 | 99.4 | <0.05 | <0.05 | <10 cfu[2]/g | <10 cfu/g |
| 1 mos. | 5.9 | 97.8 | 0.11 | 0.1 | NA[3] | NA |
| 2 mos. | 6.0 | 99.2 | <0.05 | <0.05 | NA | NA |
| 3 mos. | 6.0 | 99.7 | <0.05 | <0.05 | NA | NA |
| 6 mos. | 5.9 | 98.8 | <0.05 | <0.05 | <10 cfu/g | <10 cfu/g |

[1]Assayed percent valsartan present at specified time.
[2]cfu = colony forming units
[3]NA = not applicable As shown in Table 11, the oral liquid composition #5, of Example 3, originally including 0.4% valsartan (4 mg/mL), was stable for at least 6 months when stored under accelerated conditions of 40° C.±2° C. with no more than (NMT) 25% relative humidity in 16 oz. HDPE bottles of the container closure system. The stability assay showed 98.8% of the original valsartan was retained in the oral liquid composition over the course of the accelerated stability conditions assay for 6 months while stored in 16 oz. HDPE bottles of the container closure system.

Figure 5:
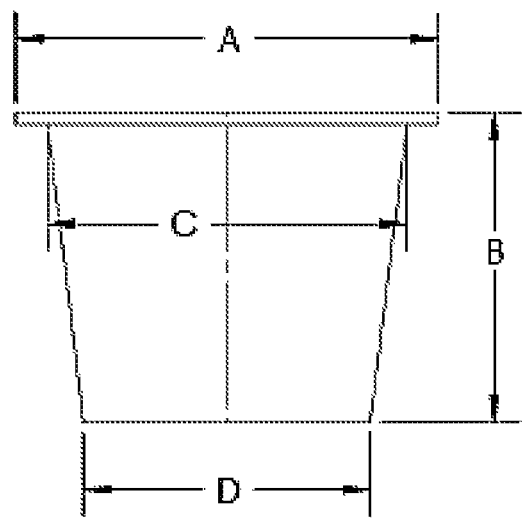
FIG. 5 is a front elevational view of a 25 mL Unit Dose Cup made of polyethylene used to contain an oral liquid composition, as described herein.

Example 6. Stability Study of the Oral Liquid Composition Containing 0.4% (4 mg/mL) Valsartan Stored in 25 mL Unit Dose Cups For purposes of conducting a stability study, the oral liquid composition #5 samples of Example 3 (20 mL), originally containing 0.4% (4 mg/mL) valsartan, were packaged in a container closure system. Each container closure system, as shown in FIG. 5, included a 25 mL unit dose cup made of HDPE (Resin: HDPE H5618; Colorant: Blue Polypropylene CPP2347) with a foil closure of 2.125" lidstock (Material: Lidding, 0.0032 PET, foil). Samples were stored in the container closure system upright under the following storage conditions: refrigerated conditions (REF) (5° C.±3° C.); controlled room temperature conditions (25° C.±2° C. and 40%±5%); intermediate conditions (INT) (35° C.±2° C. and 65%±5% RH); and accelerated conditions (ACC) (40° C.±2° C. and not more than (NMT) 25% RH.

The stability samples were stored in a calibrated stability chamber. Samples of the oral liquid composition were taken at set time intervals to assay for valsartan, pH, individual unspecified impurities, total impurities, total aerobic microbial count, and total yeast/mold count. Samples were analyzed using a High Performance Liquid Chromatography (HPLC) system equipped with a pump, autosampler, UV detector, and a suitable data acquisition system. The HPLC column used included packing L1 (C18), 5 μm, 250 mm×4.6 mm. The HPLC parameters used included 230 nm detection, a flow rate of 1.5 mL/min, an injection volume of 20 μL, run at ambient temperature, for a run time of 25 minutes using a mobile phase of acetonitrile, DI water, and glacial acetic acid (40:60:0.1).

Table 12 reports the stability data for the oral liquid composition containing, by weight, 0.4% valsartan (4 mg/mL), stored under refrigerated conditions (5° C.±3° C.) in 25 mL Unit Dose Cups, at 3, 6, 9, 12, 18, and 24 month time intervals.

TABLE 12

Stability assay for the oral liquid composition containing, by weight, 0.4% valsartan, (4 mg/mL) tested under refrigerated conditions (5° C. ± 3° C.) and stored in a 25 mL Unit Dose Cup.

| Time | pH | Valsartan[1] (%) | Individual Unspecified Impurities (%) | Total Impurities (%) | Total Aerobic Microbial Count | Total Yeast/Mold Count |
|---|---|---|---|---|---|---|
| Initial | 5.9 | 99.8 | <0.05 | <0.05 | <10 cfu[2]/g | <10 cfu/g |
| 3 mos. | 5.9 | 99.2 | 0.11 | 0.1 | NA[3] | NA |
| 6 mos. | 5.9 | 99.7 | <0.05 | <0.05 | NA | NA |
| 9 mos. | 5.9 | 99.6 | <0.05 | <0.05 | NA | NA |
| 12 mos. | 6.0 | 99.0 | <0.05 | <0.05 | NA | NA |
| 18 mos. | 6.0 | 99.0 | <0.05 | <0.05 | NA | NA |
| 24 mos. | 6.0 | 99.9 | <0.05 | <0.05 | <10 cfu/g | <10 cfu/g |

[1]Assayed percent valsartan present at specified time.
[2]cfu = colony forming units
[3]NA = not applicable As indicated in Table 12, the oral liquid composition #5, originally including 0.4% valsartan (4 mg/mL), was stable for at least 24 months when stored under refrigerated (REF) conditions of 5° C.±3° C. relative humidity in 25 mL Unit Dose Cups. The stability assay showed 99.9% of the original valsartan was retained in the oral liquid composition over the course of the refrigerated stability conditions assay for 24 months while stored in 25 mL Unit Dose Cups.

Table 13 reports the stability data for the oral liquid composition containing, by weight, 0.4% valsartan (4 mg/mL), stored under standard conditions (25° C.±2° C. and 40%±5% RH) in 25 mL Unit Dose Cup, at 3, 6, 9, 12, 18, and 24 month time intervals.

TABLE 13

Stability assay for the oral liquid composition containing, by weight, 0.4% valsartan, (4 mg/mL) tested under standard conditions (25° C. ± 2° C./40% ± 5% RH) and stored in 25 mL Unit Dose Cups.

| Time | pH | Valsartan[1] (%) | Individual Unspecified Impurities (%) | Total Impurities (%) | Total Aerobic Microbial Count | Total Yeast/ Mold Count |
|---|---|---|---|---|---|---|
| Initial | 5.9 | 99.8 | <0.05 | <0.05 | <10 cfu[2]/g | <10 cfu/g |
| 3 mos. | 5.9 | 98.1 | <0.05 | <0.05 | NA[3] | NA |
| 6 mos. | 5.9 | 100.9 | <0.05 | <0.05 | NA | NA |
| 9 mos. | 6.0 | 99.7 | <0.05 | <0.05 | NA | NA |
| 12 mos. | 6.0 | 99.7 | <0.05 | <0.05 | <10 cfu/g | <10 cfu/g |
| 18 mos. | 6.0 | 99.0 | 0.07 | 0.1 | NA | NA |
| 24 mos. | 6.0 | 99.4 | 0.1 | 0.1 | <10 cfu/g | <10 cfu/g |

[1]Assayed percent valsartan present at specified time.
[2]cfu = colony forming units
[3]NA = not applicable As indicated in Table 13, the oral liquid composition #5, originally including 0.4% valsartan (4 mg/mL), was stable for at least 24 months when stored under standard conditions (25° C.±2° C. and 40%±5% RH) in 25 mL Unit Dose Cups. The stability assay showed 99.4% of the original valsartan was retained in the oral liquid composition over the course of the standard stability conditions assay for 24 months.

Table 14 reports the stability data for the oral liquid composition #5 containing, by weight, 0.4% valsartan (4 mg/mL), stored under intermediate conditions (35° C.±2° C. and 65%±5% RH) in 25 mL Unit Dose Cups, at 3, 6, 9, 12, 18, and 24 month time intervals.

TABLE 14

Stability assay for the oral liquid composition containing, by weight, 0.4% valsartan, (4 mg/mL) tested under intermediate conditions (35° C. ± 2° C./ 65% ± 5% RH) and stored in 25 mL Unit Dose Cups.

| Time | pH | Valsartan[1] (%) | Individual Unspecified Impurities (%) | Total Impurities (%) | Total Aerobic Microbial Count | Total Yeast/ Mold Count |
|---|---|---|---|---|---|---|
| Initial | 5.9 | 99.8 | <0.05 | <0.05 | <10 cfu[2]/g | <10 cfu/g |
| 3 mos. | 5.9 | 97.8 | <0.05 | <0.05 | NA[3] | NA |
| 6 mos. | 5.9 | 98.1 | <0.05 | <0.05 | NA | NA |
| 9 mos. | 5.9 | 99.9 | <0.05 | <0.05 | NA | NA |
| 12 mos. | 5.9 | 100.5 | <0.05 | <0.05 | NA | NA |
| 18 mos. | 6.0 | 100.8 | 0.06 | 0.1 | NA | NA |
| 24 mos. | 6.0 | 98.7 | 0.07 | 0.1 | <10 cfu/g | <10 cfu/g |

[1]Assayed percent valsartan present at specified time.
[2]cfu = colony forming units
[3]NA = not applicable As shown in Table 14 above, the oral liquid composition #5, which originally included 0.4% valsartan (4 mg/mL), was stable for at least 24 months when stored under intermediate conditions (35° C.±2° C./65%±5% RH) in 25 mL Unit Dose Cups. The stability assay showed 98.7% of the original valsartan was retained in the oral liquid composition over the course of the intermediate stability conditions assay for 24 months in the 25 mL Unit Dose Cups.

Table 15 reports the stability data for the oral liquid composition containing, by weight, 0.4% valsartan (4 mg/mL), stored under accelerated conditions (40° C.±2° C. and NMT 25% RH) in 25 mL Unit Dose Cups, at 1, 2, 3, and 6 month time intervals.

TABLE 15

Stability assay for the oral liquid composition containing, by weight, 0.4% valsartan, (4 mg/mL) tested under accelerated conditions (40° C. ± 2° C./NMT 25% RH) and stored in 25 mL Unit Dose Cups.

| Time | pH | Valsartan[1] (%) | Individual Unspecified Impurities (%) | Total Impurities (%) | Total Aerobic Microbial Count | Total Yeast/ Mold Count |
|---|---|---|---|---|---|---|
| Initial | 5.9 | 99.8 | <0.05 | <0.05 | <10 cfu[2]/g | <10 cfu/g |
| 1 mos. | 5.9 | 99.4 | <0.05 | <0.05 | NA[3] | NA |
| 2 mos. | 6.0 | 99.4 | <0.05 | <0.05 | NA | NA |
| 3 mos. | 6.0 | 99.5 | <0.05 | <0.05 | NA | NA |
| 6 mos. | 5.9 | 100.3 | <0.05 | <0.05 | <10 cfu/g | <10 cfu/g |

[1]Assayed percent valsartan present at specified time.
[2]cfu = colony forming units
[3]NA = not applicable As indicated in Table 15, the oral liquid composition #5, which originally included 0.4% valsartan (4 mg/mL), was stable for at least 6 months stored under accelerated conditions (40° C.±2° C. and NMT 25% RH) in 25 mL Unit Dose Cups. The stability assay showed 100% of the original valsartan was retained in the oral liquid composition over the course of the accelerated stability conditions assay for 6 months and stored in the 25 mL Unit Dose Cups.

Example 7. A Comparative Bioequivalence Study of an Oral Liquid Composition Including Valsartan (4 mg/mL, Total of 320 mg) with a Reference Product Tablet Including Valsartan (320 mg).

A bioequivalence study was conducted on healthy, adult, human subjects under fasting conditions to assess comparative bioavailability of a single oral dose (80 mL) of an oral liquid composition including 4 mg/mL valsartan (total 320 mg) with a reference product tablet including 320 mg of valsartan.

A further objective of the bioequivalence study was to assess the safety and tolerability of a single dose (80 mL) of an oral liquid composition including valsartan (40 mg/mL, total of 320 mg valsartan) administered to healthy, adult, human subjects under fasting conditions.

Table 16 lists the ingredients combined to provide the oral liquid composition including valsartan administered to subjects in the bioequivalence study of this Example 7.

TABLE 16

Composition of the oral liquid composition including valsartan (4 mg/mL) administered in the bioequivalence study of Example 7.

| Ingredient | Amount (mg)/ dose (4 mg/mL) | Weight Percent | Batch Size (kg) |
|---|---|---|---|
| Valsartan | 4.0 | 0.40 | 0.80 |
| Potassium Sorbate | 2.0 | 0.20 | 0.40 |
| Methylparaben | 2.0 | 0.20 | 0.40 |
| Grape Flavor | 3.0 | 0.30 | 0.60 |
| Poloxamer | 10.0 | 1.0 | 2.0 |
| Sodium Citrate Dihydrate | 10.0 | 1.0 | 2.0 |
| Sucralose | 0.20 | 0.02 | 0.04 |

TABLE 16-continued

Composition of the oral liquid composition including valsartan (4 mg/mL) administered in the bioequivalence study of Example 7.

| Ingredient | Amount (mg)/ dose (4 mg/mL) | Weight Percent | Batch Size (kg) |
|---|---|---|---|
| Propylene Glycol | 100 | 10.0 | 20.0 |
| Purified Water | 868.8 | 86.9 | QS to 200 Liters |
| TOTAL | 1000.0 | 100.0 | 200 Liters |

The study was conducted with 66 healthy, adult male subjects in an age range of 18 to 45 years with a body-mass index of at least 18.5 kg/m$^2$ and not more than 24.9 kg/m$^2$, and with a body weight not less than 50 kg. Table 17 reports the demographics of the subjects participating in the bioequivalence study of Example 7.

TABLE 17

Demographic profile of the participants completing the bioequivalence study of Example 7.

|  |  | Oral Liquid Composition including Valsartan (320 mg) | Valsartan Tablet (320 mg) |
|---|---|---|---|
| Age | Mean ± SD | 28.15 ± 6.17 | 28.15 ± 6.17 |
|  | Range | 18-43 | 18-43 |
| Age Group | 18-40 | 60 (90.91%) | 60 (90.91%) |
|  | 41-64 | 06 (9.09%) | 06 (9.09%) |
| Sex | Male | 66 (100%) | 66 (100%) |
|  | Female | — | — |
| Race | Asian | 66 (100%) | 66 (100%) |
| BMI (Kg/m$^2$) | Mean ± SD | 22.87 ± 2.84 | 22.87 ± 2.84 |
|  | Range | 18.57 to 24.88 | 18.57 to 24.88 |
| Height (m) | Mean ± SD | 1.67 ± 0.05 | 1.67 ± 0.05 |
|  | Range | 1.51 to 1.77 | 1.51 to 1.77 |
| Weight (kg) | Mean ± SD | 63.63 ± 7.23 | 63.63 ± 7.23 |
|  | Range | 50.40 to 77.90 | 50.40 to 77.90 |

Treatment period one of the bioequivalence study of Example 7 included administering a single dose of 80 mL of the oral liquid composition including 4 mg/mL valsartan (a total of 320 mg valsartan) to each of the study subjects as per a randomization schedule under fasting conditions overnight (no food for at least 10 hours). Treatment period two of the study included administering a single 320 mg tablet of valsartan to the same subjects who had participated in the first treatment period as per a randomization schedule, also under fasting conditions overnight (no food for at least 10 hours). The total duration of the study was eleven days with a washout period of seven days between the first and second treatment periods. The single dose of medication was administered to the subjects in a sitting posture with 240 mL water. Standard meals of 2200-2400 kcal. were provided to subjects at 4, 8, and 13 hours post-dosing on Day 1. Drinking of water was restricted one hour before and one hour after administration of the medication, except for the 240 mL of water given at the time of administration of the medication.

Twenty five blood samples (1×5 ml) were collected in pre-labelled K2 EDTA vacutainers from each subject following administration. Single venous blood samples were withdrawn at pre-dose (t=0.00) and at 0.33, 0.66, 1.00, 1.33, 1.66, 2.00, 2.33, 2.66, 3.00, 3.33, 3.66, 4.00, 4.33, 4.66, 5.00, 5.50, 6.00, 7.00, 8.00, 10.00, 12.00, 16.00, 24.00 and 48.00 hours post-dose. The cannulation was carried out before pre-dose sample collection and was maintained until the 12.00 hour sample. After the 12.00 hour sample was withdrawn, the cannula was removed and sample collection was completed by direct venipuncture. Pre-dose blood samples were collected at a phlebotomy station, and post-dose blood samples were collected at bedside from 0.33 hrs to 8.00 hrs. Following the collection at 8.00 hours, blood samples were collected at the phlebotomy station.

Valsartan was estimated in plasma using a High Performance Liquid Chromatography Mass Spectrometric Method in Positive Ion Mode for the estimation of valsartan in human plasma using Valsartan d9 as an internal standard. Sample preparation was accomplished by Solid-Phase extraction technique. The reconstituted samples were chromatographed on Kromasil 100-5-C18, 100×4.6 mm, 5 µm column (Manufacturer: AkzoNovel, Amsterdam, Netherlands) using a mobile phase consisting of 0.1% formic acid: methanol (20:30, v/v). Pharmacokinetic parameters of $C_{max}$, $AUC_{last}$, $AUC_{inf}$, $T_{max}$, $t_{1/2}$, $K_{el}$, and AUC_% Extrap_Obs were estimated for valsartan by using Phoenix WinNonlin 6.3. Table 18 reports the pharmacokinetic parameters determined in the study of Example 7.

TABLE 18

Pharmacokinetic parameters determined in subjects participating in the bioequivalence study of the oral liquid composition including valsartan (4 mg/mL, 320 mg valsartan) and valsartan tablet (320 mg) of Example 7.

| Pharmacokinetic Parameter | Oral Liquid Composition (4 mg/mL valsartan, 320 mg) | Valsartan tablet (320 mg) |
|---|---|---|
| $T_{max}$ (hr) | 1.00 (0.66-2.66) | 4.00 (1.33-5.50) |
| $C_{max}$ (ng/mL) | 11498 (±3216) | 6606 (±3220) |
| $AUC_{last}$ (ng · hr/mL) | 52176 (±18298) | 43580 (±21528) |
| $AUC_{inf}$ (ng · hr/mL) | 53646 (±18484) | 45001 (±21857) |
| $T_{1/2}$ (hr) | 5.71 (±1.72) | 5.69 (±2.61) |
| $K_{el}$ (hr$^{-1}$) | 0.128 (±0.0258) | 0.134 (±0.032) |
| AUC_% Extrap obs | 2.89 (±1.81) | 3.55 (±2.45) |

The 90% confidence intervals for the log transformed $C_{max}$, $AUC_{last}$, and $AUC_{inf}$ of valsartan are reported in Table 19. The 90% confidence intervals of the ratio (liquid/tablet) of the least squares means for $C_{max}$, $AUC_{last}$, and $AUC_{inf}$ of valsartan form the basis for concluding the equivalence of the oral liquid composition including valsartan and the valsartan tablet. The criteria applied to conclude that the two "treatments" (administration of the oral liquid composition and administration of the valsartan tablet) are "bio-equivalent" is that the point estimate of the ratio and the confidence intervals must be entirely included in the range of 80.00% to 125.00% for $C_{max}$, $AUC_{last}$, and $AUC_{inf}$ for the log-transformed data.

TABLE 19

The 90% confidence intervals for the log transformed $C_{max}$, $AUC_{last}$, and $AUC_{inf}$ pharmacokinetic parameters for the oral liquid composition including valsartan (4 mg/mL valsartan, total 320 mg valsartan) and for the valsartan tablets (320 mg valsartan).

| Pharmacokinetic Parameters | 90% C.I. for log transformed data (%) Valsartan |
|---|---|
| $C_{max}$ (ng/mL) | 170 to 205 |
| $AUC_{last}$ (ng · hr/mL) | 115 to 137 |
| $AUC_{inf}$ (ng · hr/mL) | 114 to 136 |

As shown in Table 19, the 90% confidence intervals for the log transformed $C_{max}$, $AUC_{last}$, and $AUC_{inf}$ of valsartan are not within the 80% to 125% acceptance criteria. For example, the 90% confidence interval for the $C_{max}$ of Example 7 ranges from 170% to 205%, which is outside of the 80% to 125% acceptance range. Thus, the conclusion reached from the study of Example 7 is that the oral liquid composition including valsartan (4 mg/mL) is not bioequivalent to the valsartan 320 mg tablets when administered to healthy, adult, male subjects under fasting conditions. Additionally, in general, the safety profiles of the oral liquid composition including valsartan and the valsartan 320 mg tablets were found to be similar. During the Example 7 study, there were no reports of death or serious or unexpected adverse events.

Example 8. A Bioavailability Study of an Oral Liquid Composition Including Valsartan (4 mg/mL, a Total of 320 mg Valsartan) Following Administration to Human Subjects Under Fasting and Fed Conditions Objectives for the bioavailability study of Example 8 were to determine the effect of food on the pharmacokinetics of the oral liquid composition including valsartan (4 mg/mL, a total of 320 mg valsartan) and to determine the safety and tolerability of the oral liquid composition on subjects administered the composition.

More specifically, the study of this Example 8 was conducted to compare pharmacokinetic parameters resulting from administering an oral liquid composition including valsartan (4 mg/mL, total of 320 mg valsartan) to healthy subjects under fed and fasting conditions.

A total of eighteen healthy adult human subjects participated in Example 8. Table 20 reports the demographics of the participating subjects.

TABLE 20

Demographic profile of the participants completing the bioavailability study of Example 8.

| | | Treatment Conditions | |
|---|---|---|---|
| Category | | Fast | Fed |
| Age | Mean ± SD | 30.9 ± 4.09 | 30.9 ± 4.09 |
| | Range | 24-39 | 24-39 |
| | Median | 31 | 31 |
| | N | 18 | 18 |
| Age Groups | 18-40 | 18 (100%) | 18 (100%) |
| Gender | Male | 18 (100%) | 18 (100%) |
| Race | Asian | 18 (100%) | 18 (100%) |
| Height (meter) | Mean ± SD | 1.67 ± 0.07 | 1.67 ± 0.07 |
| | Range | 1.53-1.80 | 1.53-1.80 |
| | Median | 1.68 | 1.68 |
| Weight (kg) | Mean ± SD | 65.2 ± 7.34 | 65.2 ± 7.34 |
| | Range | 50.6-79.0 | 50.6-79.0 |
| | Median | 66.1 | 66.1 |
| BMI (kg/m$^2$) | Mean ± SD | 23.4 ± 1.87 | 23.4 ± 1.87 |
| | Range | 18.6-24.9 | 18.6-24.9 |
| | Median | 23.9 | 23.9 |

During part I of the study of Example 8, a randomized schedule initially selected nine subjects for administration of 80 mL of the oral liquid composition (including 320 mg valsartan) under fasting conditions and nine subjects for administration of the composition under fed conditions. Following the collection and analysis of blood samples from the subjects, the subjects were given a washout period of seven days. After the washout period, the subjects then participated in part II of the study of Example 8. In part II, the subjects were again administered the oral liquid composition including valsartan, but were given the composition under fed conditions if the subject had been fasting in part I, and under fasting conditions if the subject had been fed in part I.

A single dose of 80 mL of oral liquid composition including valsartan (4 mg/mL, a total of 320 mg valsartan) was administered to the subjects in a sitting posture with 240 mL water. The subjects were instructed to remain in a sitting posture for two hours following the administration of the composition.

Subjects that were fasting were administered the oral liquid composition including valsartan after at least 10 hours of overnight fasting. Following administration of the oral liquid composition including valsartan (4 mg/mL, a total of 320 mg valsartan), each fasting subject was restricted from eating for four hours. After the four-hour period, each fasting subject was provided standard meals comprising 2200-2400 kcal. at 4.00, 8.00, and 13.00 hours post dosing.

Subjects that were administered the oral liquid composition including valsartan under fed conditions initially fasted overnight for at least 10 hours and then were served a standard non-vegetarian, high-calorie, high-fat, breakfast comprising 800-1000 kcal. The subjects were asked to complete eating the breakfast within 30 minutes followed by administration of the oral liquid composition including valsartan (4 mg/mL, a total of 320 mg valsartan). After the breakfast and administration of the composition, food was restricted for four hours followed by standard meals comprising 1700-1900 kcal at 4.00, 8.00, and 13.00 hours post dosing. Other than the 240 mL of water given during the administration of the oral liquid composition, drinking water was restricted for one hour before and one hour after administration of the oral liquid composition including valsartan (4 mg/mL, 320 mg valsartan).

Blood samples (1×5 mL) were collected from each of the subjects using the method and schedule as described in Example 7. Valsartan was estimated in plasma using a High Performance Liquid Chromatography Mass Spectrometric Method in Positive Ion Mode for the estimation of valsartan in human plasma using Valsartan d9 as an internal standard. Sample preparation was accomplished by Solid-Phase extraction technique. The reconstituted samples were chromatographed on Kromasil 100-5-C18, 100×4.6 mm, 5 μm column (Make: AkzoNovel) using a mobile phase consisting of 0.1% formic acid:methanol (20:30, v/v). Pharmacokinetic parameters of $C_{max}$, $AUC_{last}$, $AUC_{inf}$, $T_{max}$, $t_{1/2}$, $K_{el}$, and AUC_% Extrap_Obs were estimated for valsartan using Phoenix WinNonlin 6.3.

Figure 6:
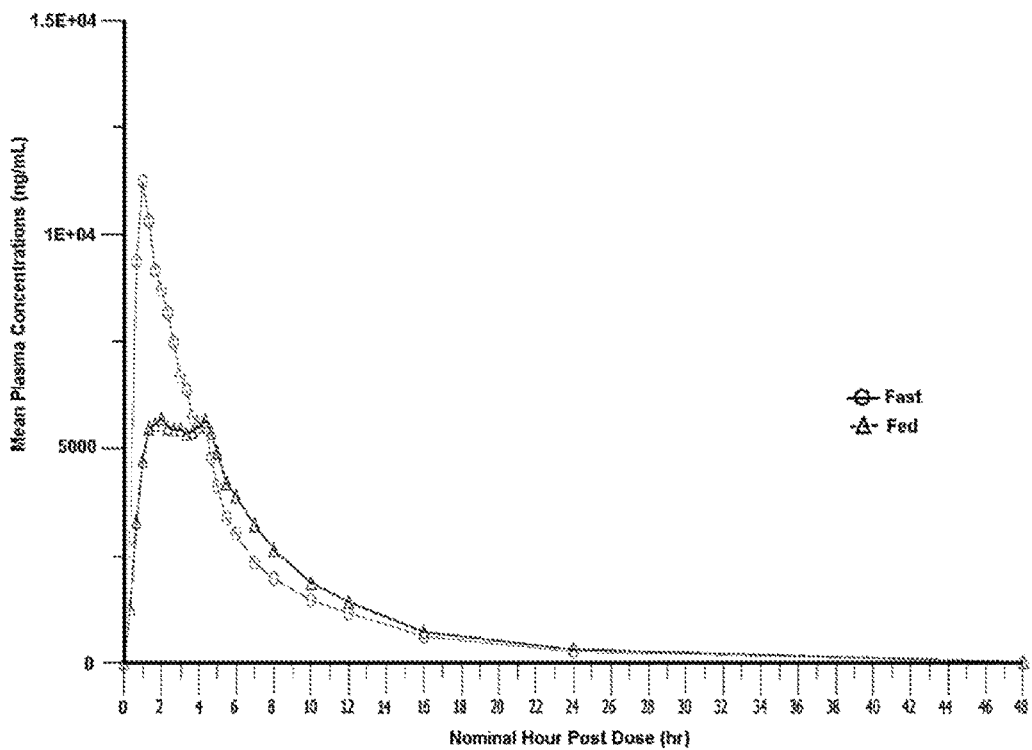
FIG. 6 is a linear plot of the valsartan mean plasma concentration versus time post administration of an oral liquid composition including valsartan (4 mg/mL, a total of 320 mg valsartan) in healthy, adult subjects under fed and fasting conditions.

FIG. 6 shows a linear plot of the valsartan mean plasma concentration versus time post administration of the oral liquid composition including valsartan (4 mg/mL, a total of 320 mg valsartan) in healthy, adult subjects under the fed and fasting conditions of Example 8. Table 21 reports the pharmacokinetic parameters determined from the blood plasma of the subjects participating in the study of Example 8.

TABLE 21

Pharmacokinetic parameters determined in subjects participating in the study of the oral liquid composition including valsartan (4 mg/mL, 320 mg valsartan) as administered to subjects under both fed and fasting conditions.
Summary of Valsartan Pharmacokinetic Results

| Parameter | $T_{max}$* (hr) | $C_{max}$ (ng/mL) | $AUC_{0-t}$ (ng · hr/mL) | $AUC_{0-\infty}$ (ng · hr/mL) | $K_{el}$ (1/hr) | $t_{1/2}$ (hr) | AUC_% Extrap_Obs |
|---|---|---|---|---|---|---|---|
| Fast | | | | | | | |
| Untransformed Mean | 1.00 | 11748 | 573988 | 591538 | 0.1158 | 6.26 | 3.03 |
| Log-Transformed Least Square Mean | — | 9.34 | 10.9 | 10.9 | — | — | — |
| Geometric Least Square Mean | — | 11402 | 56138 | 57895 | — | — | — |
| Fed | | | | | | | |
| Untransformed Mean | 2.17 | 6505 | 53206 | 55049 | 0.118 | 6.94 | 3.51 |
| Log-Transformed Least Square Mean | — | 8.76 | 10.8 | 10.9 | — | — | — |
| Geometric Least Square Mean | — | 6398 | 51708 | 53601 | — | — | — |
| Fast/Fed Ratio (%) | — | 178 | 109 | 108 | — | — | — |
| 90% CI | — | 159-199 | 99.9-118 | 99.9-117 | — | — | — |
| Intra-Subject Variability (%) | — | 19.5 | 14.4 | 13.4 | — | — | — |
| Power (%) | — | 94.8 | 99.5 | 99.8 | — | — | — |

Figure 7:
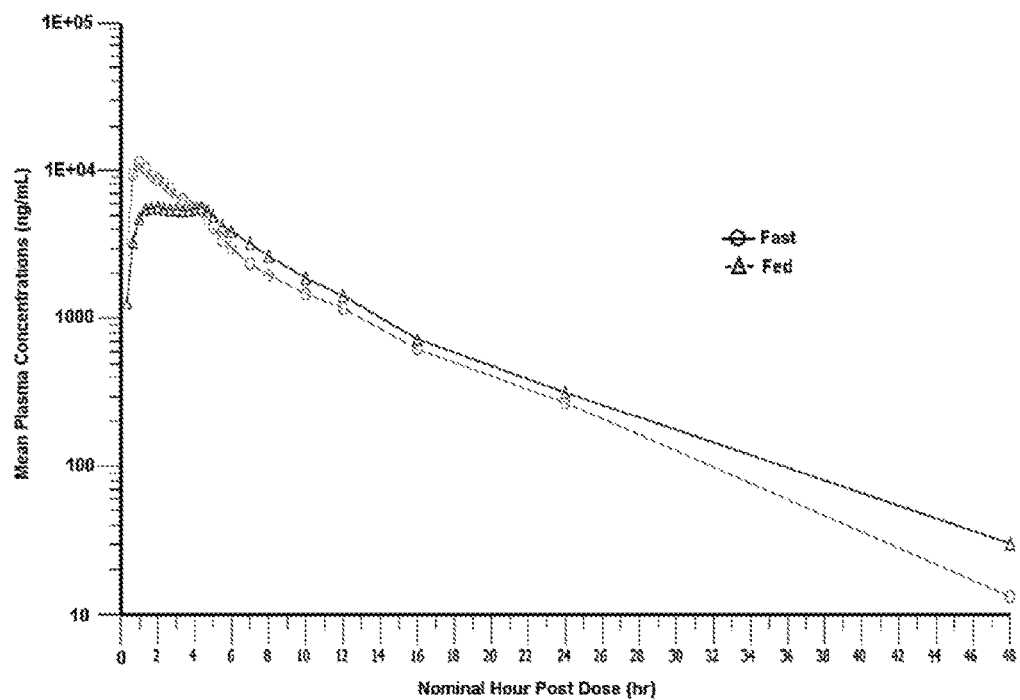
FIG. 7 is a semi-log plot of the mean plasma valsartan concentration versus time post administration of an oral liquid composition including valsartan (4 mg/mL, a total of 320 mg valsartan) in healthy, adult subjects under fed and fasting conditions.

FIG. 7 shows a semi-log plot of the mean plasma valsartan concentration versus time post administration of the oral liquid composition including valsartan (4 mg/mL, a total of 320 mg valsartan) in healthy, adult subjects under the fed and fasting conditions of Example 8. A summary of the pharmacokinetic parameters including the mean values and 90% confidence standard deviation of the mean values is provided in Table 22.

TABLE 22

Summary of the pharmacokinetic parameters determined in subjects administered the oral liquid composition including valsartan (4 mg/mL, 320 mg valsartan) under both fed and fasting conditions.

| Pharmacokinetic Parameters | Valsartan Mean (± S.D.) | |
|---|---|---|
| | Fast | Fed |
| $T_{max}$ (hr)* | 1.00 (0.66-2.00) | 2.17 (1.33-4.66) |
| $C_{max}$ (ng/mL) | 11748 (±3023.26456) | 6505 (±1226) |
| $AUC_{0-t}$ (ng · hr/mL) | 57398 (±12883) | 53205 (±13339) |
| $AUC_{0-\infty}$ (ng · hr/mL) | 59153 (±13121) | 55049 (±13232.50184) |
| $t_{1/2}$ (hr) | 6.26 (±1.4629) | 6.94 (±4.0087) |
| $k_{el}$ (1/hr) | 0.115 (±0.021) | 0.118 (±0.038) |
| AUC_% Extrap obs | 3.03 (±1.35) | 3.51 (±1.87) |

*Median (Min.-Max.)

To determine whether the oral liquid composition including valsartan (4 mg/mL, a total of 320 mg valsartan) was bioequivalent under both fasting and fed conditions, a ratio of the geometric least square mean and 90% confidence intervals for the log-transformed data was calculated. Table 23 reports the results of the bioequivalence criteria for the administration of the oral liquid composition including valsartan (4 mg/mL, a total of 320 mg of valsartan) under fast and fed conditions.

TABLE 23

Summary of the 90% confidence interval bioequivalence criteria for the administration of the oral liquid composition including valsartan (4 mg/mL, a total of 320 mg of valsartan) under fast and fed conditions.

| Parameters | Geometric Least Squares Mean | | Fast/Fed Ratio (%) | 90% Confidence Interval |
|---|---|---|---|---|
| | Fast | Fed | | |
| $C_{max}$ (ng/mL) | 11402 | 6398 | 178 | 159-199 |
| $AUC_{0-t}$ (ng * hr/mL) | 56138 | 51708 | 109 | 99.9-118 |
| $AUC_{0-\infty}$ (ng * hr/mL) | 57895 | 53601 | 108 | 99.9-117 |

The criteria applied to conclude that the oral liquid composition including valsartan administered to healthy, adult male subjects under fed conditions is "bio-equivalent" to the oral liquid composition including valsartan administered to healthy, adult male subjects under fasting conditions is that the point estimate of the ratio and the confidence intervals must be entirely included in the range of 80.00% to 125.00% for $C_{max}$, $AUC_{last}$, and $AUC_{inf}$ for the log-transformed data. As shown in Table 23, the 90% confidence intervals for the log transformed $C_{max}$, $AUC_{last}$, and $AUC_{inf}$ of valsartan are not all within the 80% to 125% acceptance criteria. For example, the 90% confidence interval for the $C_{max}$ of Example 8 ranges from 159% to 199%, which is entirely outside of the 80% to 125% acceptance range. Thus, the conclusion from the study of Example 8 is that the oral liquid composition including valsartan (4 mg/mL) administered to healthy, adult male subjects under fasting conditions is not bioequivalent to the oral liquid composition including valsartan (4 mg/mL) administered to healthy, adult male subjects under fed conditions. In general, the safety profile of the oral liquid composition including valsartan under both fasting and fed conditions was found to be similar. Further, during the Example 8 study there were no reports of death or serious or unexpected adverse events.

The following numbered clauses are directed to various non-limiting examples of compositions and methods according to the present disclosure:

1. An oral liquid composition comprising valsartan, or a pharmaceutically acceptable salt or solvate thereof, wherein administration of a 320 mg dose of the oral liquid composition to a patient provides an in vivo plasma profile having a valsartan $C_{max}$ between about 8281 ng/mL and about 14713 ng/mL.

2. An oral liquid composition comprising valsartan, or a pharmaceutically acceptable salt or solvate thereof, wherein administration of a 320 mg dose of the oral liquid composition to a patient provides an in vivo plasma profile having a valsartan $AUC_{inf}$ between about 35,162 ng*hr/mL and about 72,130 ng*hr/mL.

3. An oral liquid composition comprising valsartan, or a pharmaceutically acceptable salt or solvate thereof, wherein administration of a dose of the oral liquid composition to a patient provides an in vivo plasma profile with a valsartan $AUC_{inf}$ within a range of about 114% to about 136% of the valsartan $AUC_{inf}$ resulting from administration of an oral tablet dosage form including the same dosage of valsartan to the patient.

4. A method comprising administering an oral liquid composition including valsartan to a patient, wherein the method achieves a valsartan $C_{max}$ in the patient ranging from about 8,281 ng/mL and about 14,713 ng/mL.

5. A method comprising administering an oral liquid composition including valsartan to a patient, wherein the method achieves a valsartan $AUC_{inf}$ in the patient ranging from about 35,162 ng*hr/mL and about 72,130 ng*hr/mL.

6. A method of treating heart failure comprising administering to a patient in need thereof, regardless of whether the patient is under fasted or fed conditions, an oral liquid composition comprising valsartan, a preservative, and a sodium citrate dehydrate.

It will be understood that the present description illustrates those aspects of the invention relevant to a clear understanding of the invention. Certain aspects that would be apparent to those of ordinary skill in the art and that, therefore, would not facilitate a better understanding of the invention have not been presented in order to simplify the present description. Although only a limited number of embodiments of the present invention are necessarily described herein, one of ordinary skill in the art will, upon considering the foregoing description, recognize that many modifications and variations of the invention may be employed. All such variations and modifications of the invention are intended to be covered by the foregoing description and the following claims.

What is claimed is:

1. An oral liquid solution comprising:
   3.6 mg/mL to 4.4 mg/mL valsartan or a pharmaceutically acceptable salt or solvate thereof; and
   9.3 mg/mL to 10.7 mg/mL citrate salt;
   provided that a pH of the oral liquid solution is from 5.8 to 6.1 and the oral liquid solution exhibits a stability for 18 months;
   provided that the valsartan or the pharmaceutically acceptable salt or solvate thereof is fully solubilized in the oral liquid solution; and
   provided that administration of a 320 mg dose of the oral liquid solution to a patient provides an in vivo plasma profile having a valsartan $AUC_{inf}$ in a range from 35,162 ng*hr/mL to 72,130 ng*hr/m L.

2. The oral liquid solution of claim 1, further comprising a preservative.

3. The oral liquid solution of claim 2, wherein the preservative comprises a sorbate salt.

4. The oral liquid solution of claim 2, wherein the preservative comprises potassium sorbate.

5. The oral liquid solution of claim 2, wherein the preservative is present in a concentration ranging from 0.8 mg/mL to 3.2 mg/mL.

6. The oral liquid solution of claim 1, wherein the citrate salt comprises sodium citrate.

7. An oral liquid solution comprising:
   3.6 mg/mL to 4.4 mg/mL valsartan or a pharmaceutically acceptable salt or solvate thereof; and
   9.3 mg/mL to 10.7 mg/mL citrate salt;
   provided that a pH of the oral liquid solution is from 5.8 to 6.1 and the oral liquid solution exhibits a stability for 18 months;
   provided that the valsartan or the pharmaceutically acceptable salt or solvate thereof is fully solubilized in the oral liquid solution; and
   provided that administration of a dose of the oral liquid solution to a patient provides an in vivo plasma profile with a valsartan $AUC_{inf}$ within a range of 114% to 136% of the valsartan $AUC_{inf}$ resulting from administration of an oral tablet dosage form including the same dosage of valsartan to the patient.

8. The oral liquid solution of claim 7, further comprising a preservative.

9. The oral liquid solution of claim 8, wherein the preservative comprises a sorbate salt.

10. The oral liquid solution of claim 8, wherein the preservative comprises potassium sorbate.

11. The oral liquid solution of claim 8, wherein the preservative is present in a concentration ranging from 0.8 mg/mL to 3.2 mg/mL.

12. The oral liquid solution of claim 7, wherein the citrate salt comprises sodium citrate.

13. A method comprising:
   administering the oral liquid solution of claim 1 to a patient for treatment of hypertension, heart failure, or reduction of cardiovascular mortality, wherein the method achieves a valsartan $AUC_{inf}$ in the patient ranging from 35,162 ng*hr/mL to 72,130 ng*hr/mL.

14. The method of claim 13, wherein the oral liquid solution further comprises a preservative.

15. The method of claim 14, wherein the preservative comprises a sorbate salt.

16. An oral liquid solution comprising:
   3.6 mg/mL to 4.4 mg/mL valsartan or a pharmaceutically acceptable salt or solvate thereof; and
   9.3 mg/mL to 10.7 mg/mL citrate salt;
   provided that a pH of the oral liquid solution is from 5.8 to 6.1 and the oral liquid solution exhibits a stability for 24 months;

provided that the valsartan or the pharmaceutically acceptable salt or solvate thereof is fully solubilized in the oral liquid solution; and provided that administration of a 320 mg dose of the oral liquid solution to a patient provides an in vivo plasma profile having a valsartan $AUC_{inf}$ in a range from 35,162 ng*hr/mL to 72,130 ng*hr/mL.

17. The oral liquid solution of claim 16, further comprising a preservative.

18. The oral liquid solution of claim 17, wherein the preservative comprises a sorbate salt.

19. The oral liquid solution of claim 17, wherein the preservative comprises potassium sorbate.

20. The oral liquid solution of claim 17, wherein the preservative is present in a concentration ranging from 0.8 mg/mL to 3.2 mg/mL.

21. The oral liquid solution of claim 16, wherein the citrate salt comprises sodium citrate.

22. An oral liquid solution comprising:
   3.6 mg/mL to 4.4 mg/mL valsartan or a pharmaceutically acceptable salt or solvate thereof; and
   9.3 mg/mL to 10.7 mg/mL citrate salt;
   provided that a pH of the oral liquid solution is from 5.8 to 6.1 and the oral liquid solution exhibits a stability for 24 months;
   provided that the valsartan or the pharmaceutically acceptable salt or solvate thereof is fully solubilized in the oral liquid solution; and
   provided that administration of a dose of the oral liquid solution to a patient provides an in vivo plasma profile with a valsartan $AUC_{inf}$ within a range of 114% to 136% of the valsartan $AUC_{inf}$ resulting from administration of an oral tablet dosage form including the same dosage of valsartan to the patient.

23. The oral liquid solution of claim 22, further comprising a preservative.

24. The oral liquid solution of claim 23, wherein the preservative comprises a sorbate salt.

25. The oral liquid solution of claim 23, wherein the preservative comprises potassium sorbate.

26. The oral liquid solution of claim 23, wherein the preservative is present in a concentration ranging from 0.8 mg/mL to 3.2 mg/mL.

27. The oral liquid solution of claim 22, wherein the citrate salt comprises sodium citrate.

* * * * *